(12) United States Patent
Andrews et al.

(10) Patent No.: US 10,781,314 B2
(45) Date of Patent: Sep. 22, 2020

(54) CELLULOSE-BASED ORGANIC PIGMENTS

(71) Applicant: ANOMERA INC., Montreal (CA)

(72) Inventors: Mark P. Andrews, Westmount (CA); Timothy Morse, Montreal (CA)

(73) Assignee: ANOMERA INC., Montreal (CA)

( * ) Notice: Subject to any disclaimer, the term of this patent is extended or adjusted under 35 U.S.C. 154(b) by 0 days.

(21) Appl. No.: 15/779,891

(22) PCT Filed: Nov. 30, 2016

(86) PCT No.: PCT/CA2016/051403
§ 371 (c)(1),
(2) Date: May 30, 2018

(87) PCT Pub. No.: WO2017/091893
PCT Pub. Date: Jun. 8, 2017

(65) Prior Publication Data
US 2019/0002700 A1   Jan. 3, 2019

Related U.S. Application Data

(60) Provisional application No. 62/260,747, filed on Nov. 30, 2015.

(51) Int. Cl.
| | |
|---|---|
| C09B 67/00 | (2006.01) |
| A61Q 1/04 | (2006.01) |
| A61K 8/73 | (2006.01) |
| A61K 8/81 | (2006.01) |
| C09D 11/322 | (2014.01) |
| C09D 11/037 | (2014.01) |
| A61K 8/02 | (2006.01) |
| C09B 67/46 | (2006.01) |
| C09B 67/02 | (2006.01) |

(52) U.S. Cl.
CPC ............ *C09B 67/009* (2013.01); *A61K 8/025* (2013.01); *A61K 8/027* (2013.01); *A61K 8/731* (2013.01); *A61K 8/817* (2013.01); *A61Q 1/04* (2013.01); *C09B 67/0097* (2013.01); *C09D 11/037* (2013.01); *C09D 11/322* (2013.01); *A61K 2800/413* (2013.01); *A61K 2800/43* (2013.01); *A61K 2800/594* (2013.01); *A61K 2800/624* (2013.01)

(58) Field of Classification Search
CPC . C09B 67/009; C09B 67/0097; C09D 11/037; C09D 11/322; A61Q 1/04; A61K 8/731; A61K 8/817; A61K 8/025; A61K 8/027
See application file for complete search history.

(56) References Cited

U.S. PATENT DOCUMENTS

| | | | |
|---|---|---|---|
| 4,475,919 A | 10/1984 | Woznicki et al. | |
| 5,769,934 A | 6/1998 | Ha et al. | |
| 6,193,843 B1 | 2/2001 | Tsai et al. | |
| 8,524,261 B2 | 9/2013 | Schmidt et al. | |
| 8,932,612 B2 | 1/2015 | Park et al. | |
| 2002/0187197 A1 | 12/2002 | Caruso et al. | |
| 2004/0052742 A1 | 3/2004 | Sojka et al. | |
| 2011/0183141 A1 | 7/2011 | Beck et al. | |
| 2013/0005869 A1 | 1/2013 | Yano et al. | |
| 2016/0175812 A1* | 6/2016 | Mohammed | ........... B01J 20/262 210/688 |

FOREIGN PATENT DOCUMENTS

| | | | |
|---|---|---|---|
| CA | 2021559 | 1/1991 | |
| CA | 2524661 A1 | 12/2004 | |
| CA | 2849750 A1 | 4/2013 | |
| CN | 103304820 * | 9/2013 | .............. B01J 20/26 |
| DE | 19929109 A1 | 12/2000 | |
| GB | 417881 A | 10/1934 | |
| JP | S55102661 A | 8/1980 | |
| JP | 62-288662 A | 12/1987 | |
| JP | H0359192 A | 3/1991 | |
| JP | H03247666 A | 11/1991 | |
| JP | H0859427 | 3/1996 | |
| JP | H11-139926 A | 5/1999 | |
| JP | H11-335240 A | 12/1999 | |
| JP | 2000-309508 | 11/2000 | |
| JP | 2004-91758 | 3/2004 | |
| JP | 2004-346026 | 12/2004 | |
| JP | 2006-506351 A | 2/2006 | |
| JP | 2011-126939 | 6/2011 | |
| JP | 2011-162608 | 8/2011 | |
| JP | 2013-517352 | 5/2013 | |

(Continued)

OTHER PUBLICATIONS

Jin et al. Amino-functionalized nanocrystalline cellulose as an adsorbent for anionic dyes, Cellulose(2015) 22: 2443-2456, May 10, 2015.*
Jln et al. Amino-functionalized nanocrystalline cellulose as an adsorbent for anionic dyes, Cellulose (2015) 22:2443-2456.*
Office Action corresponding to Japanese Patent Application No. 2018-523511 dated Oct. 30, 2018.
Nishikata et al., "A Natural-Looking Makeup," Cosmetics & Toiletries, vol. 112, pp. 39-56 (May 1, 1997).
Baranoski et al., "An Introduction to Light Interaction with Human Skin," Revista de Informática Teórica e Aplicada (RITA), vol. XI, No. 1, pp. 33-62 (2004).
International Preliminary Report on Patentability with Written Opinion of the International Searching Authority and International Search Report corresponding to International Patent Application Serial No. PCT/CA2015/050707 dated Jan. 31, 2017.

(Continued)

*Primary Examiner* — Amina S Khan
(74) *Attorney, Agent, or Firm* — Jenkins, Wilson, Taylor & Hunt, P.A.

(57) ABSTRACT

A pigment comprising dyed crystalline cellulose particles comprising a crystalline cellulose core having a surface charge, optionally one or more polyelectrolyte layers with alternating charges adsorbed on top of each other on the crystalline cellulose core, the polyelectrolyte layer closest to the core having a charge opposite the surface charge of the core, and at least one organic dye having a charge is provided.

20 Claims, 12 Drawing Sheets

(56) References Cited

FOREIGN PATENT DOCUMENTS

| WO | WO 00/15420 A1 | 3/2000 |
| WO | WO 00/15720 A1 | 3/2000 |
| WO | WO 2014/138976 | 9/2014 |
| WO | WO 2014/164313 A1 | 10/2014 |

OTHER PUBLICATIONS

International Preliminary Report on Patentability and Written Opinion of the International Searching Authority corresponding to International Patent Application Serial No. PCT/CA2016/051403 dated Jun. 5, 2018.

International Search Report corresponding to International Application No. PCT/CA2016/051403 dated Jan. 25, 2017.

Nishikata et al., "A Natural-Looking Makeup," Cosmetics & Toiletries, vol. 112, pp. 39-55 (May 1, 1997).

Office Action corresponding to Canadian Patent Application Serial No. 3,002,430 dated Jun. 20, 2018.

Office Action corresponding to Canadian Patent Application Serial No. 3,002,430 dated May 18, 2018.

Chauhan et al., "A nanocellulose-dye conjugate for multi-format optical pH-sensing," Chemical Communications, vol. 50, No. 67, pp. 9493-9496 (2014).

Extended European Search Report corresponding to European Patent Application No. 16869438.8 dated Jul. 3, 2019.

* cited by examiner

CELLULOSE-BASED ORGANIC PIGMENTS

CROSS REFERENCE TO RELATED APPLICATIONS

This application claims benefit, under 35 U.S.C. § 371, of PCT International Patent Application Serial No. PCT/CA2016/051403, filed Nov. 30, 2016, incorporated herein by reference in its entirety, which claims benefit, under 35 U.S.C. § 119(e), of U.S. provisional application Ser. No. 62/260,747, filed Nov. 30, 2015.

FIELD OF THE INVENTION

The present invention relates to cellulose based organic pigments. More specifically, the present invention is concerned with organic pigments based on crystalline cellulose and methods of manufacture thereof.

BACKGROUND OF THE INVENTION

The term "pigment" applies to colorants that are insoluble in the application medium, the vehicle, in which they are used. Typical examples of organic pigments are phthalocyanines, azo pigments, diketopyrrolopyrroles and quinacridones. Inorganic pigments include various iron oxides, chromium oxides and metal sulfides. Pigments are distinguished from dyes, which are soluble in the vehicle in which they are used.

Pigments can exhibit higher chemical and photochemical stability than dyes. Soluble dyes can be converted into pigments by precipitating the soluble dye after combining it with a metal ion to make an insoluble salt. The resulting pigment is generally referred to as a lake pigment.

Pigments for use in cosmetics must be converted to a form that enables easy dispersal and reproducible color in various media, like oils and waxes. Grinding is one way to achieve these properties. Indeed, grinding increases the surface area and visual effect of a pigment. However, grinding often requires the addition of a wetting agent which can modify the color of the pigment. Furthermore, grinding crucially affects the quality of the end product, including its feel.

It is known in the cosmetics industry that desirable feel can be imparted to cosmetic materials by adding fillers. In particular, spherical silica ($SiO_2$) and poly(methylmethacrylate) (PMMA) particles are employed as fillers in cosmetics to impart a natural appearance to human skin and to make wrinkles less visible.

The importance of using pigments to match color cosmetics to skin color and tone is known to consumers. But there is a need for a cosmetic foundation that gives the user a natural look, that provides a natural sheen that resembles or duplicates the look of healthy skin, i.e. healthy glow and natural color. Nevertheless, it is difficult to have a foundation cosmetic that simultaneously covers skin flaws, creates even skin tones and yields the healthy and vibrant glow of clean and clear skin. These desirable properties are difficult to satisfy simultaneously.

One reason is that the inorganic compounds like titanium dioxide and iron oxide pigments used to provide desirable color and coverage are mainly opaque, and this obscures the intended vibrancy, often imparting a chalky look to light skin and an ashy look to dark skin, especially under ultraviolet, fluorescent and even natural light. Pearlescent pigments that are incorporated to impart sheen often give an unnatural look to the skin. Even color pigments that are incorporated to match skin tone often provide a dull matte appearance and therefore cannot match the look and glow of healthy normal skin. Sometimes ingredients like emolients are added to impart sheen, but this benefit changes over time because the composition is mobile on the skin, wipes off or changes its composition due to the secretion of sebum.

Much research has been devoted to understanding the optical properties of skin. These studies have focused on absorption, scattering, transmittance, reflection and the spatial energy distribution of light. Sometimes spherical particles are coated with a layer that imparts color. A pigment mixture that incorporates spherical $SiO_2$ particles exhibiting high light scattering has also been disclosed. Some of the particles are coated with $TiO_2$ and some are coated with $Fe_2O_3$. Such fillers are known to have relatively good skin feel. However, they have the disadvantage of a white, unnatural appearance on the skin. This is due in part to the fact that the presence of surface particles on the spheres increases light scattering or attenuates (absorbs) light.

Recently, there has been a shift towards pigments based solely on organic ingredients, especially those which are compatible with aqueous formulations. Inorganic pigments currently dominate the market in terms of volume, but the organic pigments market is growing rapidly. There is a need for new types of pigments based on organic ingredients derived, in part or in whole, from renewable resources. Organic pigments are expected to be non-toxic, biodegradable alternatives to currently used inorganic pigments. While the market for organic pigments is growing, the variety of products available remains limited, and many suffer from poor lightfastness, which results in fading over time.

The different solubility or dispersibility of pigments and dyes can make it difficult to produce colors that span the CIE color space chromicity diagram. There is a need to make pigments that can be combined (blended) without concern for different solubility or dispersibility of pigments and dyes.

Organic personal care products, sometimes called green personal care products, are desirable in order to address increasing consumer concerns regarding personal health and hygiene. Limited shelf life, raw material supply and stringent regulatory restrictions are key challenges to overcome to provide such products. Strong awareness about the efficacy of organic personal care products and lifestyle changes are important motivators for consumers to adopt green personal care products, including cosmetics based on them.

On another subject, cellulose is a widely used substance in personal care products, including some cosmetics. It is also a broadly available raw material with a long shelf life depending on its formulation. Cellulose is considered a sustainable-sourced material. Cellulose is a semi-crystalline organic polymer, a polysaccharide that is produced naturally as a structural material of the cell wall of plants, algae and some fungus-like micro-organisms. Cellulose is naturally organized into long linear chains of linked poly($\beta$-1,4-glucopyranose) units that assemble by strong intra- and inter-molecular hydrogen bonds into highly crystalline fibrils with amorphous regions within the fibrils. Extensive hydrogen bonding among the cellulose polymer chains makes cellulose extremely resistant to dissolution in water. Cellulose materials and dispersions of them have been widely used as an excipient in drug tablets, and as a thickener and stabilizer in cosmetics and processed foods.

By breaking chemical bonds in the amorphous regions, cellulose can be converted to cellulose nanocrystals, also called nanocrystalline cellulose (NCC). Nanocrystalline cellulose can thus be produced from cellulose by strong acid hydrolysis of the amorphous components of wood pulp and other biomaterials, where the amorphous regions of cellulose in the pulp are destroyed to liberate the nanocrystals. When NCC is prepared by acid hydrolysis using concentrated sulfuric acid, it contains sulfate esters. The sulfuric acid method can yield crystallites of fairly uniform size. Hydrochloric, hydrobromic and mixed acetic-nitric acids are also capable of hydrolysing cellulose to yield NCC without adding ester functionalities to the surface. Inorganic persulfates, like ammonium persulfate, can produce nanocrystalline cellulose that contains varying amounts of a carboxylic acid (—COOH) group. Hydrogen peroxide can produce nanocrystalline cellulose that contains varying amounts of a carboxylic acid (—COOH) group. The carboxylic acid group can also be introduced by a process called TEMPO oxidation or by periodate oxidation.

SUMMARY OF THE INVENTION

In accordance with the present invention, there is provided:
1. a pigment comprising dyed crystalline cellulose particles comprising:
   a crystalline cellulose core having a surface charge,
   optionally one or more polyelectrolyte layers with alternating charges adsorbed on top of each other on the crystalline cellulose core, the polyelectrolyte layer closest to the core having a charge opposite the surface charge of the core, and
   at least one organic dye having a charge,
   wherein:
   A) when the charge of the organic dye is opposite the surface charge of the crystalline cellulose core,
      1) the organic dye is directly adsorbed on the surface of the crystalline cellulose core without intervening polyelectrolyte layers, or
      2) the organic dye is adsorbed on an even number of polyelectrolyte layers with alternating charges, and
   B) when the charge of the organic dye is the same as the surface charge of the crystalline cellulose core, the organic dye is adsorbed on an odd number of polyelectrolyte layers with alternating charges.
2. The pigment as described above, wherein the charge of the organic dye is opposite the surface charge of the crystalline cellulose core and the organic dye is directly adsorbed on the surface of the crystalline cellulose core without intervening polyelectrolyte layers.
3. The pigment as described above, wherein the crystalline cellulose core has a negative surface charge and the organic dye has a positive charge.
4. The pigment as described above, wherein the crystalline cellulose core has a positive surface charge and the organic dye has a negative charge.
5. The pigment as described above, wherein the charge of the organic dye is opposite the surface charge of the crystalline cellulose core and the organic dye is adsorbed on an even number of polyelectrolyte layers with alternating charges adsorbed on top of each other on the crystalline cellulose core, the polyelectrolyte layer closest to the core having a charge opposite the surface charge of the core.
6. The pigment as described above wherein the number of polyelectrolyte layers with alternating charges is 2.
7. The pigment as described above, wherein the crystalline cellulose core has a negative surface charge, the polyelectrolyte layer closest to the core has a positive charge, the next polyelectrolyte layer has a negative charge and the organic dye has a positive charge.
8. The pigment as described above, wherein the crystalline cellulose core has a positive surface charge, the polyelectrolyte layer closest to the core has a negative charge, the next polyelectrolyte layer has a positive charge and the organic dye has a negative charge.
9. The pigment as described above, wherein the charge of the organic dye is the same as the surface charge of the crystalline cellulose core and the organic dye is adsorbed on an odd number of polyelectrolyte layers with alternating charges adsorbed on top of each other on the crystalline cellulose core, the polyelectrolyte layer closest to the core having a charge opposite the surface charge of the core.
10. The pigment as described above, wherein the number of polyelectrolyte layers with alternating charges is 1.
11. The pigment as described above, wherein the crystalline cellulose core has a negative surface charge, the polyelectrolyte layer has a positive charge, and the organic dye has a negative charge.
12. The pigment as described above, wherein the crystalline cellulose core has a positive surface charge, the polyelectrolyte layer has a negative charge, and the organic dye has a positive charge.
13. The pigment as described above, wherein the crystalline cellulose core comprises microcrystalline cellulose.
14. The pigment as described above, wherein the crystalline cellulose core comprises positively-charged microcrystalline cellulose.
15. The pigment as described above, wherein the microcrystalline cellulose is microcrystalline cellulose modified with glycidyltrimethylammonium chloride functional groups, or with adsorbed cationic amylopectin.
16. The pigment as described above, wherein the crystalline cellulose core comprises negatively-charged microcrystalline cellulose.
17. The pigment as described above, wherein the microcrystalline cellulose is microcrystalline cellulose with phosphate and polyphosphate functional groups, carboxymethylcellulose sodium salt, carboxymethyl cellulose sodium sulfate salt, and microcrystalline cellulose reacted with calcium alginate.
18. The pigment as described above, wherein the crystalline cellulose core comprises a particle of microcrystalline cellulose.
19. The pigment as described above, wherein the crystalline cellulose core comprises nanocrystalline cellulose.
20. The pigment as described above, wherein the crystalline cellulose core comprises positively-charged nanocrystalline cellulose.
21. The pigment as described above, wherein the nanocrystalline cellulose is nanocrystalline cellulose with glycidyltrimethylammonium chloride functional groups, nanocrystalline cellulose reacted cationic surfactant hexadecyltrimethylammonium or cationic polyacrylamide or nanocrystalline cellulose grafted with a cationic polymer such as aminoethylmethacrylate and aminoethylmethacrylamide.
22. The pigment as described above, wherein the crystalline cellulose core comprises negatively charged nanocrystalline cellulose.
23. The pigment as described above, wherein the nanocrystalline cellulose is carboxylated nanocrystalline cellulose, sulfonated nanocrystalline cellulose, phosphonated nanocrystalline cellulose, or a salt thereof.
24. The pigment as described above, wherein the nanocrystalline cellulose is carboxylated nanocrystalline cellulose or a salt thereof.

25. The pigment as described above, wherein the nanocrystalline cellulose is nanocrystalline cellulose sodium carboxylate.
26. The pigment as described above, wherein the nanocrystalline cellulose is sulfonated nanocrystalline cellulose or a salt thereof.
27. The pigment as described above, wherein the crystalline cellulose is nanocrystalline cellulose sodium sulfonate.
28. The pigment as described above, wherein the crystalline cellulose core comprises nanocrystalline cellulose made of cellulose nanocrystals having dimensions in width of about 2 to about 20 nm and in length of about 80 to about 250 nm.
29. The pigment as described above, wherein the cellulose nanocrystals have dimensions in width of about 5 to about 10 nm and in length of about 150 to about 200 nm.
30. The pigment as described above, wherein the crystalline cellulose core comprises a nanocrystal of nanocrystalline cellulose.
31. The pigment as described above, wherein the dyed crystalline cellulose comprises a negatively-charged polyelectrolyte.
32. The pigment as described above, wherein the polyelectrolyte is a copolymer of acrylamide with acrylic acid or a copolymer comprising 2-acrylamido-2-methyl-propane sulphonic acid sodium salt.
33. The pigment as described above, wherein the dyed crystalline cellulose comprises a positively-charged polyelectrolyte.
34. The pigment as described above, wherein the polyelectrolyte is a copolymer of acrylamide with an aminoderivative of acrylic acid or methacrylic acid ester; quaternized poly-4-vinylpyridine; poly-2-methyl-5-vinylpyridine; poly(ethyleneimine); pol-L-lysine, a poly(amidoamine); a poly(amino-co-ester), or a polyquaternium.
35. The pigment as described above, wherein the polyelectrolyte is a polyquaternium.
36. The pigment as described above, wherein the polyelectrolyte is polyquaternium-6.
37. The pigment as described above, wherein the dyed crystalline cellulose comprises a positively-charged dye.
38. The pigment as described above, wherein the dye is Red dye #2GL, Light Yellow dye #7GL.
39. The pigment as described above, wherein the dyed crystalline cellulose comprises a negatively-charged dye.
40. The pigment as described above, wherein the dye is D&C Red dye #28, FD&C Red dye #40, FD&C Blue dye #1 FD&C Blue dye #2, FD&C Yellow dye #5, FD&C Yellow dye #6, FD&C Green dye #3, D&C Orange dye #4, D&C Violet dye #2, phloxine B (D&C Red dye #28), and Sulfur Black #1
41. The pigment as described above, wherein the dye is a D&C dye.
42. The pigment as described above, wherein the dye is a FD&C dye.
43. The pigment as described above, wherein the dyed crystalline cellulose particles comprise more than one dye simultaneously.
44. The pigment as described above, comprising a mixture of dyed crystalline cellulose particles of at least two different hues.
45. The pigment as described above, wherein the dyed crystalline cellulose particles are mixed with undyed crystalline cellulose particles comprising:
    the crystalline cellulose core, and
    optionally one or more polyelectrolyte layers with alternating charges adsorbed on top of each other on the crystalline cellulose core, the polyelectrolyte layer closest to the core having a charge opposite the surface charge of the core,
    wherein the undyed crystalline cellulose particles are free of dyes.
46. The pigment as described above, wherein the crystalline cellulose particles are aggregated into aggregates.
47. The pigment as described above, wherein the aggregates are spherical.
48. The pigment as described above, wherein the aggregates are not spherical.
49. The pigment as described above, wherein the aggregates have an average size up to about 50 microns.
50. The pigment as described above, wherein the crystalline cellulose particles are suspended in a fluid.
51. The pigment as described above, wherein the crystalline cellulose particles are suspended in water.
52. The pigment as described above, wherein the pigment is in the form of a powder.
53. An ink comprising the pigment as described above suspended in a liquid.
54. A cosmetic preparation comprising the pigment as described above and a cosmetically acceptable auxiliary agent.
55. A method of producing a pigment comprising dyed crystalline cellulose particles, the method comprising the steps of:
    a) providing crystalline cellulose cores having a surface charge, an organic dye having a charge, optionally a first polyelectrolyte having a charge opposite to the charge of the crystalline cellulose cores, and optionally a second polyelectrolyte having the same charge as the crystalline cellulose cores,
    when the charge of the organic dye is opposite the surface charge of the crystalline cellulose core,
        b) optionally adsorbing an even number of polyelectrolyte layers with alternating charges on top of each other on the crystalline cellulose core, and then
        c) adsorbing the organic dye on the crystalline cellulose core, thereby producing the pigment,
    or when the charge of the organic dye is the same as the surface charge of the crystalline cellulose core
        b') adsorbing an odd number of polyelectrolyte layers with alternating charges on top of each other on the crystalline cellulose core, and then
        c') adsorbing the organic dye on the crystalline cellulose core, thereby producing the pigment,
    wherein the polyelectrolyte layer closest to the core has a charge opposite the surface charge of the core.
56. The method as described above, wherein step b) is present
57. The method as described above, wherein step b) comprises:
    b1) suspending the crystalline cellulose cores in a liquid in which the first polyelectrolyte is soluble, adding the first polyelectrolyte dye to the suspension, thereby adsorbing the first polyelectrolyte on the surface of the crystalline cellulose core,
    b2) isolating the crystalline cellulose cores,
    b3) suspending the crystalline cellulose cores in a liquid in which the second polyelectrolyte is soluble, adding the second polyelectrolyte dye to the suspension, thereby adsorbing the second polyelectrolyte on the surface of the crystalline cellulose core, and
    b4) isolating the crystalline cellulose cores, and
    b5) optionally repeating all of steps b1) to b4) one or more times.

58. The method as described above, wherein step b) is absent.
59. The method as described above, wherein step b') comprises:
   b'1) suspending the crystalline cellulose cores in a liquid in which the second polyelectrolyte is soluble, adding the first polyelectrolyte dye to the suspension, thereby adsorbing the second polyelectrolyte on the surface of the crystalline cellulose core, and
   b'2) isolating the crystalline cellulose cores.
60. The method of as described above, wherein step b') further comprises:
   b'3) suspending the crystalline cellulose cores in a liquid in which the first polyelectrolyte is soluble, adding the first polyelectrolyte dye to the suspension, thereby adsorbing the first polyelectrolyte on the surface of the crystalline cellulose core,
   b'4) isolating the crystalline cellulose cores,
   b'5) optionally, suspending the crystalline cellulose cores in a liquid in which the second polyelectrolyte is soluble, adding the second polyelectrolyte dye to the suspension, thereby adsorbing the second polyelectrolyte on the surface of the crystalline cellulose core,
   b'6) isolating the crystalline cellulose cores, and
   b'7) optionally repeating all of steps b'3) to b'6) one or more times.
61. The method as described above, wherein steps c) and/or c') comprise the steps of suspending the crystalline cellulose cores in a liquid in which the dye is soluble, and adding the dye to the suspension, thereby adsorbing the organic dye directly on the surface of the crystalline cellulose core.
62. The method as described above, wherein the liquid in steps b1), b3), b'1), b'3, and/or b'5) is water.
63. The method as described above, wherein in steps c) and/or c'), two or more different dyes are added.
64. The method as described above, further comprising the step d) of isolating/purifying the pigment.
65. The method as described above, further comprising the step e) of mixing the dyed crystalline cellulose particles with dyed crystalline cellulose particles of a different hue.
66. The method as described above, further comprising the step f) of mixing the dyed crystalline cellulose particles with undyed crystalline cellulose particles, the undyed crystalline cellulose particles comprising:
   the crystalline cellulose core, and
   optionally one or more polyelectrolyte layers with alternating charges adsorbed on top of each other on the crystalline cellulose core, the polyelectrolyte layer closest to the core having a charge opposite the surface charge of the core,
   the undyed crystalline cellulose particles being free of dyes.
67. The method as described above, further comprising the step g) of suspending the dyed crystalline cellulose particles in a liquid.
68. The method as described above, wherein the liquid is water.
69. The method as described above, further comprising the step h) of aggregating the dyed crystalline cellulose particles, thereby producing aggregates.
70. The method as described above, further comprising the step i) of drying the pigment to form a powder.
71. The method as described above, wherein the pigment is as defined above.

DETAILED DESCRIPTION OF THE INVENTION

Figure 1:
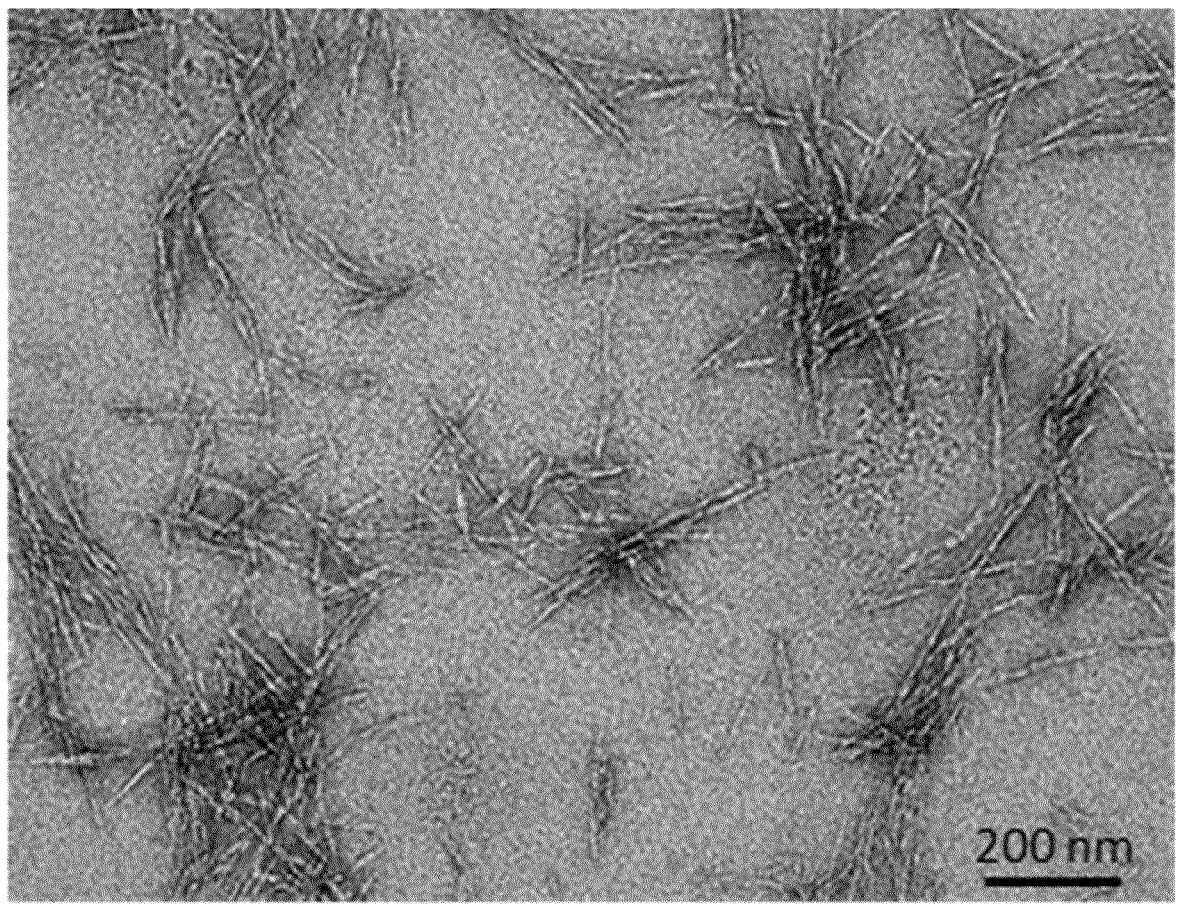
FIG. 1 is a transmission electron micrograph of carboxylated nanocrystalline cellulose.

Turning now to the invention in more details, there is provided a pigment, and more specifically a new type of organic pigment.

Herein, a pigment is a substance that imparts a color to a medium in which it is incorporated. The pigment is insoluble in the medium. Therefore, the pigment will be incorporated into a fluid medium as a suspension. The pigment can also be provided as a powder that is to be mixed with a solid medium.

The pigment of the invention comprises dyed crystalline cellulose particles. These particles comprise:
   a crystalline cellulose core having a surface charge,
   optionally one or more polyelectrolyte layers with alternating charges adsorbed on top of each other on the crystalline cellulose core, the polyelectrolyte layer closest to the core having a charge opposite the surface charge of the core, and
   at least one organic dye having a charge, wherein:
A) when the charge of the organic dye is opposite the surface charge of the crystalline cellulose core,
   1) the organic dye is directly adsorbed on the surface of the crystalline cellulose core without intervening polyelectrolyte layers, or
   2) the organic dye is adsorbed on an even number of polyelectrolyte layers with alternating charges, and
B) when the charge of the organic dye is the same as the surface charge of the crystalline cellulose core, the organic dye is adsorbed on an odd number of polyelectrolyte layers with alternating charges, The core surface charge and the charges of the organic dye and polyelectrolytes are due to various functional groups called electrolyte groups. Non-limiting examples of functional groups that can produce a positive charge include amines. These include primary amines (—$NH_2$) and secondary amines (—NRH) as well as tertiary amines (—$NR_2$), olefinic amines such as classes of allyl amine and various classes of mono- and polycyclic nitrogen and heterocycles, such as imidazole (for example, 1-butyl-3-methylimidazolium chloride) and triazole. Non-limiting examples of functional groups that can dissociate to produce a negative charge include carboxylic acids (—COOH) as well as organic phosphonic acids (—$PO(OH)_2$), including bisphosphonates, amino- and carboxyphosphonates, and organic sulfonic acids (—$SO_2OH$) and combinations of these.

The organic dye, the optional polyelectrolyte layers, and the core are adsorbed on top of each other via electrostatic interaction due to their mutually opposite charges (this is why the polyelectrolyte layer closest to the core has a charge opposite the surface charge of the core.) This is advantageous, as the various components of the particles are strongly adsorbed together, without necessitating covalent bonds. This arrangement results in a pigment that is typically stable in water, while involving only electrostatic interactions.

In A1) above, either a negative dye ($D^-$) is adsorbed directly onto the surface of a core with a positive charge ($C^+$) or a positively charged dye ($D^+$) is adsorbed directly onto the surface of a core with a negative charge ($C^-$). These two embodiments can be be noted as follows, respectively:
   Positive core and negative dye: ($C^+$)-($D^-$)
   Negative core and positive dye: ($C^-$)-($D^+$)

A2) and B) above involve even and odd numbers of polyelectrolyte layers of alternating charges, respectively. These alternating changes means that when one polyelectrolyte layer is of a given charge, the polyelectrolyte layer below it (if any) and the polyelectrolyte layer above it (if any) will have the opposite charge.

In A2), the even number of polyelectrolyte (PE) layers of alternating charges results in a particle with a surface with the same charge as the core surface (which may be positive or negative) and on which the dye (that has a charge opposite that of the core surface and thus also opposite that of the last PE layer) can be adsorbed. Here are a few examples, with the lowest possible number of PE layers for these embodiments (2 and 4):
   Two PE layers on a positively charged core: ($C^+$)-($PE^-$)-($PE^+$)-($D^-$)
   Four PE layers on a positively charged core: ($C^+$)-($PE^-$)-($PE^+$)-($PE^-$)-($PE^+$)-($D^-$)
   Two PE layers on a negatively charged core: ($C^-$)-($PE^+$)-($PE^-$)-($D^+$)
   Four PE layers on a negatively charged core: ($C^-$)-($PE^+$)-($PE^-$)-($PE^+$)-($PE^-$)-($D^+$)

In B), the odd number of PE layers of alternating charges results in a particle surface with a charge opposite that of the core surface (which may be positive or negative) and on which the dye (with has the same charge as the core surface and thus a charge opposite that of the last PE layer) can be adsorbed. Here are a few example, with the lowest possible number of PE layers for these embodiments (1 and 3):
   One PE layer on a positively charged core: ($C^+$)-($PE^-$)-($D^+$)
   Three PE layers on a positively charged core: ($C^+$)-($PE^-$)-($PE^+$)-($PE^-$)-($D^+$)
   One PE layer on a negatively charged core: ($C^-$)-($PE^+$)-($D^-$)
   Three PE layers on a negatively charged core: ($C^-$)-($PE^+$)-($PE^-$)-($PE^+$)-($D^-$)

In preferred embodiments in which the charge of the organic dye is opposite the surface charge of the crystalline cellulose core, the organic dye is directly adsorbed on the surface of the crystalline cellulose core without intervening polyelectrolyte layers, and/or the organic dye is adsorbed on two (2) polyelectrolyte layers with alternating charges.

In preferred embodiments in which the charge of the organic dye is the same as the surface charge of the crystalline cellulose core, the organic dye is adsorbed on a single polyelectrolyte layer having a charge opposite the surface charge of the core. In yet more preferred embodiments, the crystalline cellulose core has a negative charge, the polyelectrolyte layer has a positive charge, and the organic dye has a negative charge. In more preferred embodiments, the crystalline cellulose core has a positive charge, the polyelectrolyte layer has a negative charge, and the organic dye has a positive charge.

Crystalline Cellulose Core

The pigment of the invention comprises a cellulose crystalline core.

In embodiments, the whole core consists (i.e. is entirely comprised) of crystalline cellulose. In other embodiments, the core rather comprises crystalline cellulose, optionally together with one or more further components. Non-limiting examples of further components include a component that can be regarded as amorphous (disordered), as in disordered cellulose. For example the crystallite may contain regions in the interior that are partially disordered, or the exterior of the crystalline cellulose may be surrounded in part or in whole by an amorphous cellulose layer.

In any and all embodiments, the size of the cellulose crystalline core may vary from the nanometer range (i.e. about 1 nm) to the micrometer range (i.e. up to about 500 μm).

The surface charge of the core will be positive or negative depending on the functional groups present at its surface. These in turn will depend on the method of manufacture of the cellulose crystalline as well as any subsequent modifications thereto.

In preferred embodiments of any and all of the above, the crystalline cellulose is nanocrystalline cellulose or microcrystalline cellulose. In more preferred embodiments, the crystalline cellulose is nanocrystalline cellulose. In other preferred embodiments, the crystalline cellulose is microcrystalline cellulose.

Microcrystalline Cellulose

Microcrystalline cellulose is a purified, partially depolymerized cellulose that is in the form of a crystalline powder composed of porous particles. It is commercially available under several tradenames such as Avicel™, Emocel™, and Vivacel™. Microcrystalline cellulose is available in different particle sizes. Typical average particles sizes range from about 20 to about 200 μm.

In embodiments of any and all of the above, the cellulose crystalline core is one microcrystalline cellulose particle.

In embodiments, the microcrystalline cellulose is positively charged. Non-limiting examples of such microcrystalline cellulose include those that can be modified by means of glycidyltrimethylammonium chloride functional groups, or by adsorption of cationic amylopectin.

In embodiments, the microcrystalline cellulose is negatively charged. Non-limiting examples of such microcrystalline cellulose include those having phosphate and polyphosphate functional groups that can be synthesized by reacting, for example, Avicel PH101, with $H_3PO_4$ as the phosphorylating agent. Other examples include the sodium salt of carboxymethylcellulose, and the sodium sulfate salt of carboxymethyl cellulose or the microcrystalline cellulose reacted with calcium alginate as in the commercial product Avicel® PC 815 Microcrystalline Cellulose.

Nanocrystalline Cellulose

Nanocrystalline cellulose is composed of cellulose nanocrystals. These are the highly crystalline particles freed from the amorphous regions in raw cellulose or cellulose processed as pulp or derived from biological sources such as bacteria, algae or tunicates. Depending on its method of manufacture, nanocrystalline cellulose can have nanocrystals of various sizes and present various surface functional groups. In embodiments, the nanocrystalline cellulose is comprised of cellulose nanocrystals having dimensions in width of about 2 to about 20 nm and in length, about 80 to about 250 nm, for example dimensions in width of about 5 to about 10 nm and in length, about 150 to about 200 nm.

In embodiments of any and all of the above, the cellulose crystalline core is one such cellulose nanocrystal.

In embodiments, the nanocrystalline cellulose is positively charged. Non-limiting examples of such nanocrystalline cellulose include those having glycidyltrimethylammonium chloride functional groups or those that are synthesized by reaction with the cationic surfactant hexadecyltrimethylammonium (HDTMA) or cationic polyacrylamide or by rendering the negative surface charge of NCC positive (see below) after grafting with cationic polymers via well-known surface-initiated living radical polymerization methods. Thus, aminoethylmethacrylate and aminoethylmethacrylamide can be polymerized on the surface of NCC to produce a cationic surface.

In a preferred embodiment, the nanocrystalline cellulose is negatively charged. Non-limiting examples of such nanocrystalline cellulose include those having carboxylate, sulfonate and phosphonate functional groups. Typically, such functionalized nanocrystalline cellulose is white in color. Nanocrystalline cellulose with sulfonate functional groups can be obtained by the well-known sulfuric acid hydrolysis method. Nanocrystalline cellulose with carboxylate functional groups can be synthesized as described in PCT patent application no. PCT/CA2015/050707, which is incorporated herein by reference.

In preferred embodiments, the crystalline cellulose is carboxylated nanocrystalline cellulose, or sulfonated nanocrystalline cellulose, or a salt thereof.

Carboxylated nanocrystalline cellulose is nanocrystalline cellulose-bearing carboxyl (—COOH) surface functional groups. A transmission electron micrograph of carboxylated nanocrystalline cellulose is shown in FIG. 1. In embodiments, the carboxylated nanocrystalline cellulose is salified to make a nanocrystalline cellulose carboxylate salt. For example, reaction with sodium hydroxide will transform at least part of the carboxylic groups into sodium carboxylate (—COO$^-$ $^+$Na) groups (hereinafter referred to as nanocrystalline cellulose sodium carboxylate).

Figure 2:
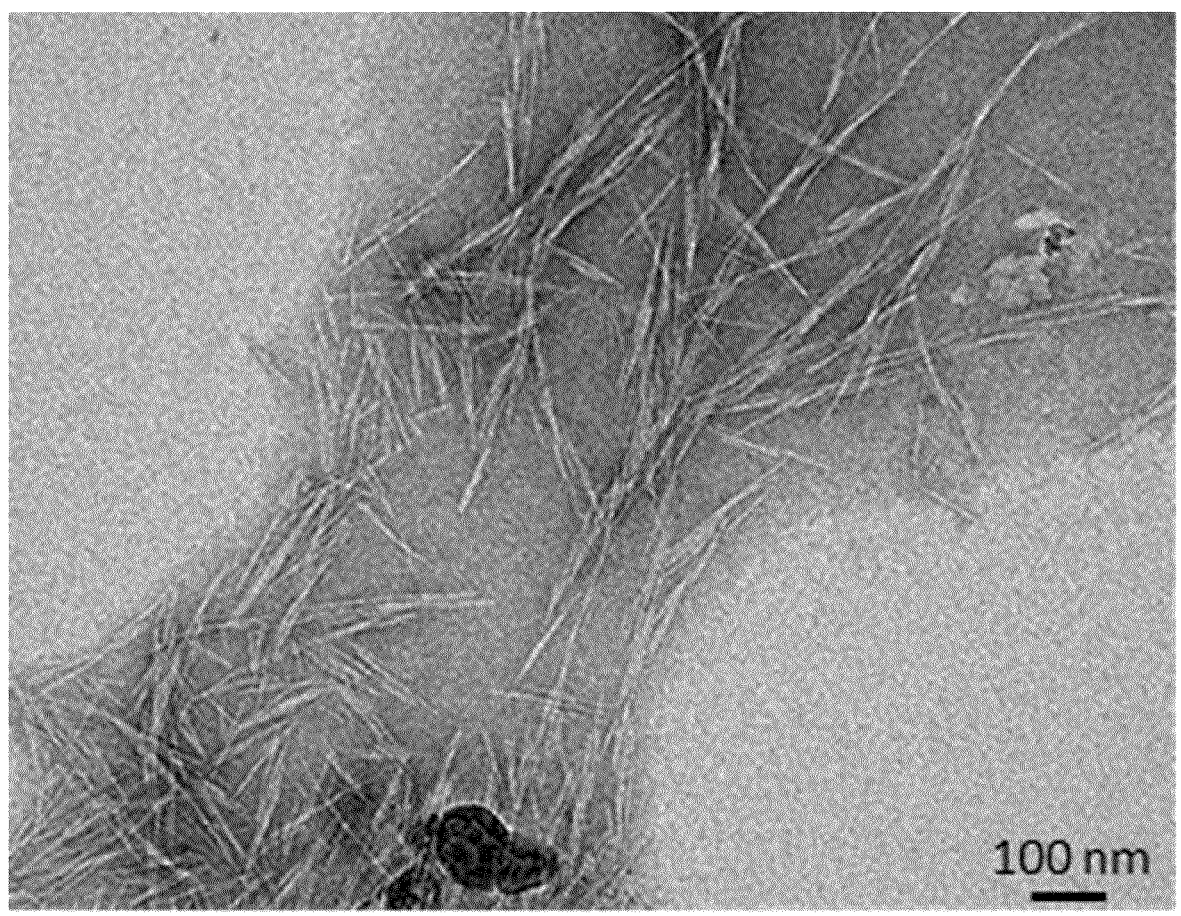
FIG. 2 is a transmission electron micrograph of sulfonated nanocrystalline cellulose.

Similarly, sulfonated nanocrystalline cellulose is nanocrystalline cellulose-bearing sulfonyl (—OSOOH) surface functional groups. A transmission electron micrograph of sulfonated nanocrystalline cellulose is shown in FIG. 2. In embodiments, the sulfonated nanocrystalline cellulose is salified to make a nanocrystalline cellulose sulfonate salt. For example, reaction with sodium hydroxide will transform at least part of the sulfonic acid groups into sodium sulfonate (—OSOO$^-$ $^+$Na) groups (hereinafter referred to as nanocrystalline cellulose sodium sulfonate).

Polyelectrolyte Layers

Polyelectrolytes are polymers (or copolymers) comprising repeating units bearing an electrolyte functional group. These groups can dissociate in aqueous solutions, making the polymers charged. Generally speaking, any water-soluble polyelectrolyte may be used in the present invention.

Polycations are positively charged polyelectrolytes, while polyanions are negatively charged polyelectrolytes.

In embodiments, the negatively charged polyelectrolyte bears electrolyte groups such as carboxylate and sulfonate. Non-limiting examples of such polyelectrolytes include copolymers of acrylamide with acrylic acid and copolymers with sulphonate-containing monomers, such as the sodium salt of 2-acrylamido-2-methyl-propane sulphonic acid (AMPS, trademark: The Lubrizol Corporation).

Preferred negatively charged electrolyte groups include sulfonate, carboxylate, and phosphonate. Preferred polyelectrolytes bearing such groups include copolymers of acrylamide with acrylic acid and copolymers with sulphonate containing monomers, such as the sodium salt of 2-acrylamido-2-methyl-propane sulphonic acid.

In embodiments, the positively charged (i.e. cationic) polyelectrolyte bears electrolyte groups such as quaternary ammonium centers amines. Cationic copolymers can be produced in a similar fashion to anionic copolymers by copolymerising acrylamide with varying proportions of amino derivatives of acrylic acid or methacrylic acid esters. Other examples include quaternized poly-4-vinylpyridine and poly-2-methyl-5-vinylpyridine.

Non-limiting examples of such cationic polyelectrolytes include poly(ethyleneimine), pol-L-lysine, poly(amidoamine)s and poly(amino-co-ester)s.

Other non-limiting examples are polyquaterniums. "Polyquaternium" is the International Nomenclature for Cosmetic Ingredients (INCI) designation for several polycationic polymers that are used in the personal care industry. INCI has approved different polymers under the polyquaternium designation. These are distinguished by the numerical value that follows the word "polyquaternium". Polyquaterniums are identified as polyquaternium-1, -2, -4, -5 to -20, -22, -24, -27 to -37, -39, -42, -44 to -47. A preferred polyquaternium is polyquaternium-6, which corresponds to poly(diallyldimethylammonium chloride).

Organic Dye

Herein, a dye is a colored substance that imparts a color to a medium in which it is incorporated. Generally speaking, in contrast to pigments, dyes are soluble in the media in which they are used. Dyes can be said to be solvent soluble, coloured, ionising and aromatic organic compounds that show an affinity to bind towards a substrate to which the dye is applied. Herein, the dye is an organic dye, i.e. a carbon-based dye, rather than a mineral-based dye.

Any organic dye may be used in the invention. More specifically, any one dye or combination or sub-combination of dyes or classes of dyes discussed below can be used.

Dyes known to be useful in the cosmetic and printing industries are contemplated.

The majority of natural dyes are from plant sources— roots, berries, bark, leaves, wood, fungi, and lichens. Mineral dyes are also common. Natural dyes may be derived from natural sources like *Punica granatum* (Natural Yellow 7) and Annatto Bixa orellana (Natural Orange). A great number of synthetic dyes are also known and, to a great extent, have replaced the natural dyes.

Dyes may be acidic, basic, direct, reactive or azoic.

Acid dyes are water-soluble anionic dyes that are typically applied to fibers such as silk, wool, nylon and modified acrylic fibers. Most synthetic food colors fall in this category. Acid dyes are typically salts of a sulfuric, carboxylic or phenolic organic acid. The salts are often sodium or ammonium salts.

Basic dyes are water-soluble cationic dyes that are mainly applied to acrylic fibers, but find some use for wool and silk. Basic dyes are also used in the coloration of paper.

Direct dyes are generally used on cotton, paper, leather, wool, silk and nylon. They are also used as pH indicators and as biological stains. They are generally set by hydrogen bonding.

Reactive dyes utilize a chromophore attached to a substituent that is capable of directly reacting with the substrate to be dyed. The covalent bonds that attach reactive dye to the substrate make them among the most permanent of dyes. "Cold" reactive dyes, such as Procion MX, Cibacron F, and Drimarene K, are very easy to use because the dye can be applied at room temperature. Reactive dyes are by far the best choice for dyeing cotton and other cellulose fibers at home or in the art studio. Wool is also dyeable with reactive dyes.

Azoic dyeing is a technique in which an insoluble azo dye is produced directly onto or within the substrate to be dyed. This is achieved by treating a substrate with both diazoic and coupling components. With suitable adjustment of dyebath conditions, the two components react to produce the required insoluble azo dye. This technique of dyeing is unique, in that the final color is controlled by the choice of the diazoic and coupling components.

One other class of dyes is the food dye. Because food dyes are classified as food additives, they are manufactured to a higher standard than some industrial dyes. Food dyes can be direct, mordant and vat dyes. Many are azo dyes, although anthraquinone and triphenylmethane compounds are used for colors such as green and blue. Some naturally-occurring dyes are also used. Thus, the dye may be a FD&C dye or a D&C dye. A FD&C dye is one of a limited number of dyes that have been approved by the Food and Drug Administration in the United-States for use in food, drugs and cosmetic. The dye may also be a D&C dye, which one of a broader, but still limited, number of dyes that have been approved by the Food and Drug Administration (FDA) in the United-States for use in drugs and cosmetics.

Dyes for inkjet printing may be used. These may be chosen, for example, from Reactive Red 180, Acid Red 52, Acid Blue 9, Direct Blue 199, Acid Yellow 23, Direct Black 168 and Direct Black 19.

Dyes typically used in water-based inks for flexographic and gravure printers can also be used.

In preferred embodiments of any and all of the above, the dye is positive.

Non-limiting examples of positively charged dyes include: Red dye #2GL, Light Yellow dye #7GL.

In preferred embodiments of any and all of the above, the dye is negative.

Non-limiting examples of negatively charged dyes include: D&C Red dye #28, FD&C Red dye #40, FD&C Blue dye #1 FD&C Blue dye #2, FD&C Yellow dye #5, FD&C Yellow dye #6, FD&C Green dye #3, D&C Orange dye #4, D&C Violet dye #2, phloxine B (D&C Red dye #28), and Sulfur Black #1. Preferred dyes include phloxine B (D&C Red dye #28), FD&C blue dye #1, and FD&C yellow dye #5.

There can be more than one dye simultaneously bound to the same dyed crystalline cellulose particles. Indeed, binding a mixture of two or more organic dyes on such particles allows the production of pigments with a larger number of hues. For example, binding both a blue dye and a yellow dye simultaneously on the same crystalline cellulose particles allows production of a green pigment. Therefore, in embodiments, the dyed crystalline cellulose particles of the pigment of the invention comprise more than one dye.

Mixtures of Various Undyed and/or Dyed Crystalline Cellulose Particles

Another way of producing pigments with a larger number of hues is to mix together dyed crystalline cellulose particles of different hues. For example, mixing blue crystalline cellulose particles with yellow crystalline cellulose particles allows production of a green pigment. Therefore, in embodiments, the pigment of the invention comprises a mixture of dyed crystalline cellulose particles of at least two different hues.

For some applications, it may be advantageous to mix the dyed crystalline cellulose particles with undyed crystalline cellulose particles. Undyed crystalline cellulose particles are the same as the dyed crystalline cellulose particles described herein except that they are free of dyes, and optionally also free of polyelectrolytes. In other words, the undyed crystalline cellulose particles comprise the crystalline cellulose core and optionally the polyelectrolyte(s) adsorbed onto the core.

Formulations

In embodiments, the pigment is provided in a form where the crystalline cellulose particles are suspended in a liquid, such as water, an organic solvent, an oil or a wax.

In other embodiments, the pigment is provided in dry form, i.e. in the form of a powder.

Potential Applications and Uses

The above suspensions and powders can be used in various applications. For example, the above suspensions and powders can be used as inks for printing and in a variety of cosmetic applications. In fact, in embodiments, the organic pigments of the invention are useful for imparting color to cosmetic formulations and printing inks as well as for coloration of organic materials, including high molecular weight organic materials.

Therefore, there is also provided an ink comprising the pigment of the invention suspended in a liquid, such as water.

Therefore, there is also provided herein a composition preparation comprising the pigment of the invention, typically with one or more cosmetically acceptable auxiliary agents.

The form of the cosmetic preparation can be any form normally used for cosmetics such as cream, emulsion, foam, gel, lotion, milk, mousse, solution, stick, ointment, paste, powder (loose or pressed), cream-to-cosmetic, spray, or suspension.

The cosmetic composition can be any colored cosmetic used on the skin, hair, eyes, or lips, such as concealing sticks, foundation (wet or dry), stage make-up, mascara (cake or cream), eye shadow (liquid, pomade, powder, stick, pressed or cream), hair color, lipsticks, lip gloss, kohl pencils, eye liners, blushers, eyebrow pencils, and cream powders. Other exemplary cosmetic compositions include, but are not limited to, nail enamel, skin glosser stick, hair sprays, face powder, leg-makeup, insect repellent lotion, nail enamel remover, perfume lotion, and shampoos of all types (gel or liquid). In addition, the compositions can be used in shaving cream (concentrate for aerosol, brushless, lathering), hair grooming, cologne stick, cologne, cologne emollient, bubble bath, body lotion (moisturizing, cleansing, analgesic, astringent), after-shave lotion, after-bath milk and sunscreen lotion.

The amount of the pigment of the invention present in a cosmetic preparation is dependent on the color cosmetic being created and the final form of the cosmetic. More pigment can be used to create higher intensity, or provide higher coverage or correction. One skilled in the art will be able to determine the appropriate amount of pigment to use based upon the desired properties of the colored cosmetic formulation.

The cosmetic preparation optionally comprises at least one cosmetically acceptable auxiliary agent. Cosmetically acceptable auxiliary agents include, but are not limited to, carriers, excipients, emulsifiers, surfactants, preservatives, fragrances, perfume oils, thickeners, polymers, gel formers, dyes, absorption pigments, photoprotective agents, consistency regulators, antioxidants, antifoams, antistats, resins, solvents, solubility promoters, neutralizing agents, stabilizers, sterilizing agents, propellants, drying agents, opacifiers, cosmetically active ingredients, hair polymers, hair and skin conditioners, graft polymers, water-soluble or dispersible silicone-containing polymers, bleaches, care agents, colorants, tinting agents, tanning agents, humectants, refatting agents, collagen, protein hydrolyzates, lipids, emollients and softeners, tinting agents, tanning agents, bleaches, keratin-hardening substances, antimicrobial active ingredients, photofilter active ingredients, repellant active ingredients, hyperemic substances, keratolytic and keratoplastic substances, antidandruff active ingredients, antiphlogistics, keratinizing substances, active ingredients which act as antioxidants and/or as free-radical scavengers, skin moisturizing or humectants substances, refatting active ingredients, deodorizing active ingredients, sebostatic active ingredients, plant extracts, antierythematous or antiallergic active ingredients and mixtures thereof.

In an aspect of the invention, the pigment is simply added to a prior art composition to enhance its aesthetic appearance. In embodiments, the pigment may provide fluid and even pasty preparations with a slight increase in apparent solidity (thixotropy). This should improve the application behavior of the preparation. For example, the slightly thixotropic function of the pigment significantly should improve the application behavior of preparations on the skin. This should allow preparing high viscosity creams, e.g. solid foundations, that have desirable spreadability on the skin and/or have good removal behavior.

Method of Production

In another aspect of the invention, a method for producing a pigment, such as the above pigment, is provided. This method comprises the steps of:
  a) providing crystalline cellulose cores having a surface charge, an organic dye having a charge, optionally a first polyelectrolyte having a charge opposite to the charge of the crystalline cellulose cores, and optionally a second polyelectrolyte having the same charge as the crystalline cellulose cores, when the charge of the organic dye is opposite the surface charge of the crystalline cellulose core,
  b) optionally adsorbing an even number of polyelectrolyte layers with alternating charges on top of each other on the crystalline cellulose core, and
  c) adsorbing the organic dye on the crystalline cellulose core, thereby producing the pigment, or when the charge of the organic dye is the same as the surface charge of the crystalline cellulose core
  b') adsorbing an odd number of polyelectrolyte layers with alternating charges on top of each other on the crystalline cellulose core, and
  c') adsorbing the organic dye on the crystalline cellulose core, thereby producing the pigment, wherein the polyelectrolyte layer closest to the core has a charge opposite the surface charge of the core.

This method takes advantage of the fact that, as surprisingly found by the present inventors, a dye can be used to successfully produce pigment particles from crystalline cellulose.

In embodiments, optional step b) is absent.

In other embodiments, optional step b) is present. In preferred embodiments where this step is present, step b) comprises:
  b1) suspending the crystalline cellulose cores in a liquid in which the first polyelectrolyte is soluble, adding first polyelectrolyte dye to the suspension, thereby adsorbing the first polyelectrolyte on the surface of the crystalline cellulose core,
  b2) isolating the crystalline cellulose cores,
  b3) suspending the crystalline cellulose cores in a liquid in which the second polyelectrolyte is soluble, adding the second polyelectrolyte dye to the suspension, thereby adsorbing the second polyelectrolyte on the surface of the crystalline cellulose core,
  b4) isolating the crystalline cellulose cores, and
  b5) optionally repeating all of steps b1) to b4) one or more times.

In embodiments, step b') comprises:
  b'1) suspending the crystalline cellulose cores in a liquid in which the second polyelectrolyte is soluble, adding the first polyelectrolyte dye to the suspension, thereby adsorbing the second polyelectrolyte on the surface of the crystalline cellulose core, and
  b'2) isolating the crystalline cellulose cores.

In embodiments, step b') further comprises:
  b'3) suspending the crystalline cellulose cores in a liquid in which the first polyelectrolyte is soluble, adding the first polyelectrolyte dye to the suspension, thereby adsorbing the first polyelectrolyte on the surface of the crystalline cellulose core,
  b'4) isolating the crystalline cellulose cores,
  b'5) optionally, suspending the crystalline cellulose cores in a liquid in which the second polyelectrolyte is soluble, adding the second polyelectrolyte dye to the suspension, thereby adsorbing the second polyelectrolyte on the surface of the crystalline cellulose core,
  b'6) isolating the crystalline cellulose cores, and
  b'7) optionally repeating all of steps b'3) to b'6) one or more times.

In embodiments, steps c) and/or c') comprise the steps of suspending the crystalline cellulose cores in a liquid in which the dye is soluble, and adding the dye to the suspension, thereby adsorbing the organic dye directly on the surface of the crystalline cellulose core.

In embodiments, one or more, preferably all, of the liquids for suspending the crystalline cellulose cores are water.

In embodiments, in steps c) and/or c'), two or more different dyes are added. As noted above, this allows producing pigments of many different hues. This particular embodiment of the method of the invention takes advantage of the fact that, as surprisingly found by the present inventors, more than one type of dye can be bound simultaneously to crystalline cellulose particles and used to successfully produce pigment exhibiting various hues.

In embodiments, the method further comprises the step d) of isolating/purifying the pigment. This can be carried out by any means known to the skilled person. Non-limiting examples include filtration, centrifugation, spray drying, freeze drying, and supercritical drying.

In embodiments, the method further comprises the step e) of mixing the dyed crystalline cellulose particles with dyed crystalline cellulose particles of a different hue. This method takes advantage of the fact that, as surprisingly found by the present inventors, dyed crystalline cellulose particles of various colors can be mixed and used to successfully produce pigments exhibiting various hues.

In embodiments, the method further comprises the step f) of mixing the dyed crystalline cellulose particles with undyed crystalline cellulose particles as defined above.

In embodiments, the method further comprises the step g) of suspending the dyed crystalline cellulose particles in a liquid, thereby providing a suspension. In embodiments, the liquid in this suspension is water. As discussed above, this suspension may directly be used in some applications, such as inks and cosmetics.

In embodiments, the method further comprises the step h) of drying the pigment to form a powder. As discussed above, this powder may directly be used in some applications. In embodiments, this step is carried out by spray-drying, which typically produces spherical aggregates. When starting with nanocrystalline cellulose, these spherical aggregates typically have an average size of up to about 50 microns. Other drying methods include freeze-drying, flash drying, and vacuum drying, which typically produces irregularly shaped aggregates.

In embodiments, the method further comprises, as needed, the step i) of milling the powder, using for example a mill or a blender, to obtain aggregates of a desired size.

In embodiments, the method further comprises the step j) of suspending the powder in a liquid. In embodiments, the liquid in this suspension is water. As discussed above, this suspension may be used in some applications, such as inks and cosmetics.

Advantages

In embodiments, the pigments and method of the invention may present one or more of the following advantages.

The pigments are desirably organic.

The pigments can be provided in the form of spherical aggregates of an average size of up to about 50 microns by spray drying, without further grinding.

The pigments are stable in water and other solvents generally. In particular, the dye does not significantly detach from the crystalline cellulose. Also, in these conditions, the particles tend to retain their shape.

Pigment of various hues can be produced simply by binding two or more dyes onto the crystalline cellulose particles and/or using together dyes of crystalline cellulose particles of various hues. Indeed, the pigments can be combined (blended or mixed) without concern for difference in solubility or dispersibility of the original dyes. This can be achieved because, in the present invention, the different dyes are bound to the same insoluble substrate simultaneously and/or different particles made from the same insoluble substrate are blended together. In this way, the pigments of the invention can desirably span the entire CIE color space chromaticity.

When prepared by spray-drying, the pigments have an enhanced feel (because of their shape and size) without the use of grinding. This is desirable, as grinding tends to modify the color of pigments.

Besides good skin feel, the pigments have good dispersibility in cosmetic formulations, chemical and photochemical stability, and a pure color. Moreover, the pigments exhibit a soft and even appearance on the skin when applied to the skin as a pure white powder, in creams, emulsions and the like.

It is desired that the pigments act as diffusers, reflectors and refractors of light in order to provide the look of skin having a uniform surface topogaphy (reduced look of wrinkles and lines) whilst providing a natural healthy glow, the illusion of sheerness and translucency that imitates the sheen of natural skin. These effects should be achieved by a composition of a pigment of the invention matched to a desired skin tone. Preferably, the pigment comprises (A) undyed crystalline cellulose particles and (B) dyed crystalline cellulose particles benchmarked to a natural skin tone and in the form of spherical aggregates that act as diffusers, reflectors and refractors.

Definitions

Any and all combinations and subcombinations of the embodiments and features disclosed herein are encompassed by the present invention. For example, any and all combinations and sub-combinations of dyed crystalline cellulose particles, crystalline cellulose cores, polyelectrolyte layers, polyelectrolyes, and dyes are encompassed.

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

Materials: Hydrogen peroxide (30% and 50%) was obtained from Fisher Chemicals (Thermo Fisher Scientific, Waltham, Mass.). Sheets of softwood spruce fiber (Temalfa93) were obtained from Tembec Inc., Temiscamingue, QC, Canada.

Example 1—Production of Carboxylated NCC with Adsorbed Polyelectrolyte

Carboxylated NCC (cNCC)

A solution of 30% $H_2O_2$ in water (2.5 L) was heated to reflux. 200 g of softwood spruce fiber sheets (Temalfa93) were cut into ~1 cm×5 cm strips and added to the boiling $H_2O_2$ solution. This mixture was stirred vigorously for 8 hours by a combination of manual and mechanical mixing due to the high viscosity at the beginning of the reaction. The reaction produced a white suspension of carboxylated NCC (cNCC) that settled when stirring was stopped. The reaction was stopped by adding ice to dilute to 4 L.

Following reaction, carboxylated NCC was purified by diafiltration using a 10 kDa hollow fiber filter from Spectrum Labs. Once the conductivity of the permeate was below 100 µS/cm, the cNCC solution was neutralized with NaOH and sonicated for 5-20 mins at 80-100% output using a Sonics Vibra-cell VCX130. Diafiltration was again used until the conductivity of the permeate reached <20 µS/cm. The suspension was then concentrated and collected.

Carboxylated NCC particle dimensions were determined by TEM after staining with uranyl acetate. Long dimensions ranged between 150-200 nm, with widths ranging between 5-10 nm.

Wide angle XRD revealed that the d-spacing resembles that of crystalline cellulose I.

The FTIR spectrum of the produced carboxylated NCC exhibits a band associated with the carboxylic acid (C=O) stretching mode at 1732 $cm^{-1}$.

Spray drying was performed by using an SD 3.5 Pilot Plant spray dryer on-site at Techni Process North America Inc. The inlet temperature was set to 175° C., with an outlet temperature of 68° C. Compressed air pressure was set at 50 psi resulting in approximately 10 L/h of feed flow to the dryer.

Figure 3:
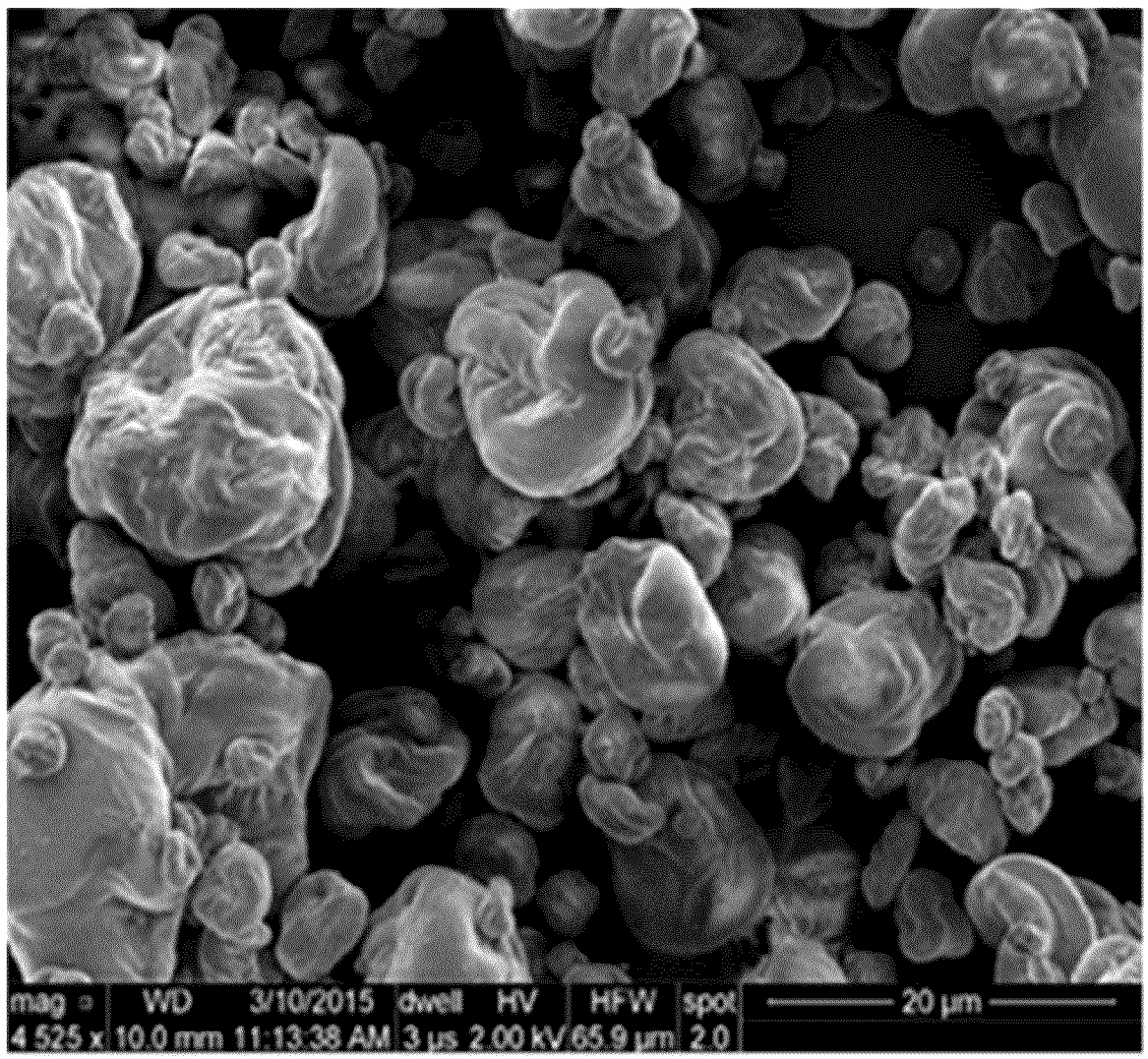
FIG. 3 is a scanning electron micrograph of pristine (white, undyed) spherical aggregates of nanocrystalline cellulose.

FIG. 3 is the scanning electron micrograph of the pristine (white, undyed) spherical aggregate of nanocrystalline cellulose obtained.

Figure 9:
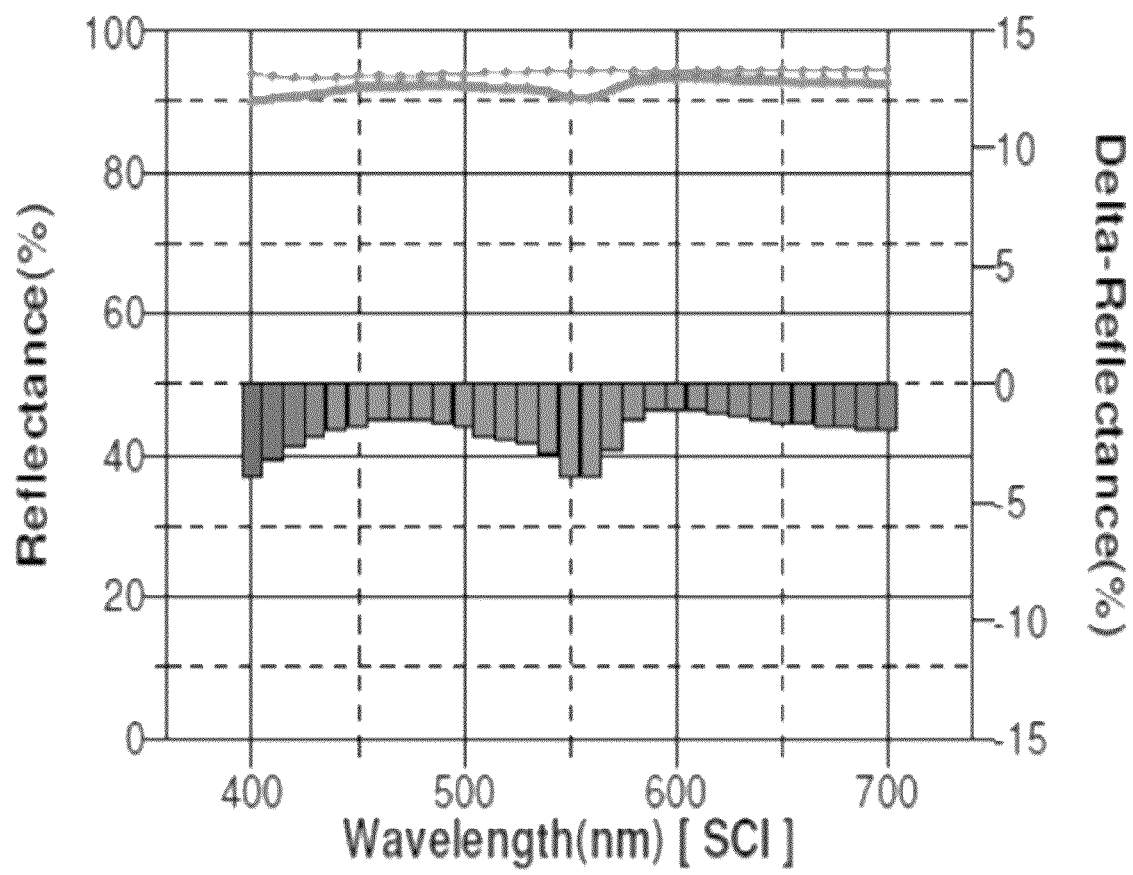
FIG. 9 is the reflectance spectrum of pristine (white, undyed) spherical aggregates of nanocrystalline cellulose.

FIG. 9 is the reflectance spectrum of the pristine (white, undyed) spherical aggregate of nanocrystalline cellulose.

Polyelectrolyte Adsorption (NCC+)

A 1 L suspension of the above cNCC in water (0.5% w/v, 5 g) was equipped with a stir bar and a Sonics Vibra-cell VCX130 probe sonicator. The suspension was stirred and sonication turned on at 100% output. Immediately following this, 35 mL of a solution of polyquaternium salt as the polydiallyldimethylammonium chloride (PDDA, also called polyquaternium-6, 400-500 kDa Mw) in water (2% w/v, 0.7 g) was rapidly added all at once to the cNCC. Sonication was continued for 40 min to yield a stable viscous suspension.

This product was purified by diafiltration using a 10 kDa MW cut-off filter until conductivity of the permeate was <20 µS/cm. This yielded a stable translucent suspension of positively charged NCC particles (NCC+).

Spray drying was performed by using an SD 3.5 Pilot Plant spray dryer on-site at Techni Process North America Inc. The inlet temperature was set to 175° C., with an outlet temperature of 68° C. Compressed air pressure was set at 50 psi resulting in approximately 10 L/h of feed flow to the dryer.

Figure 4:
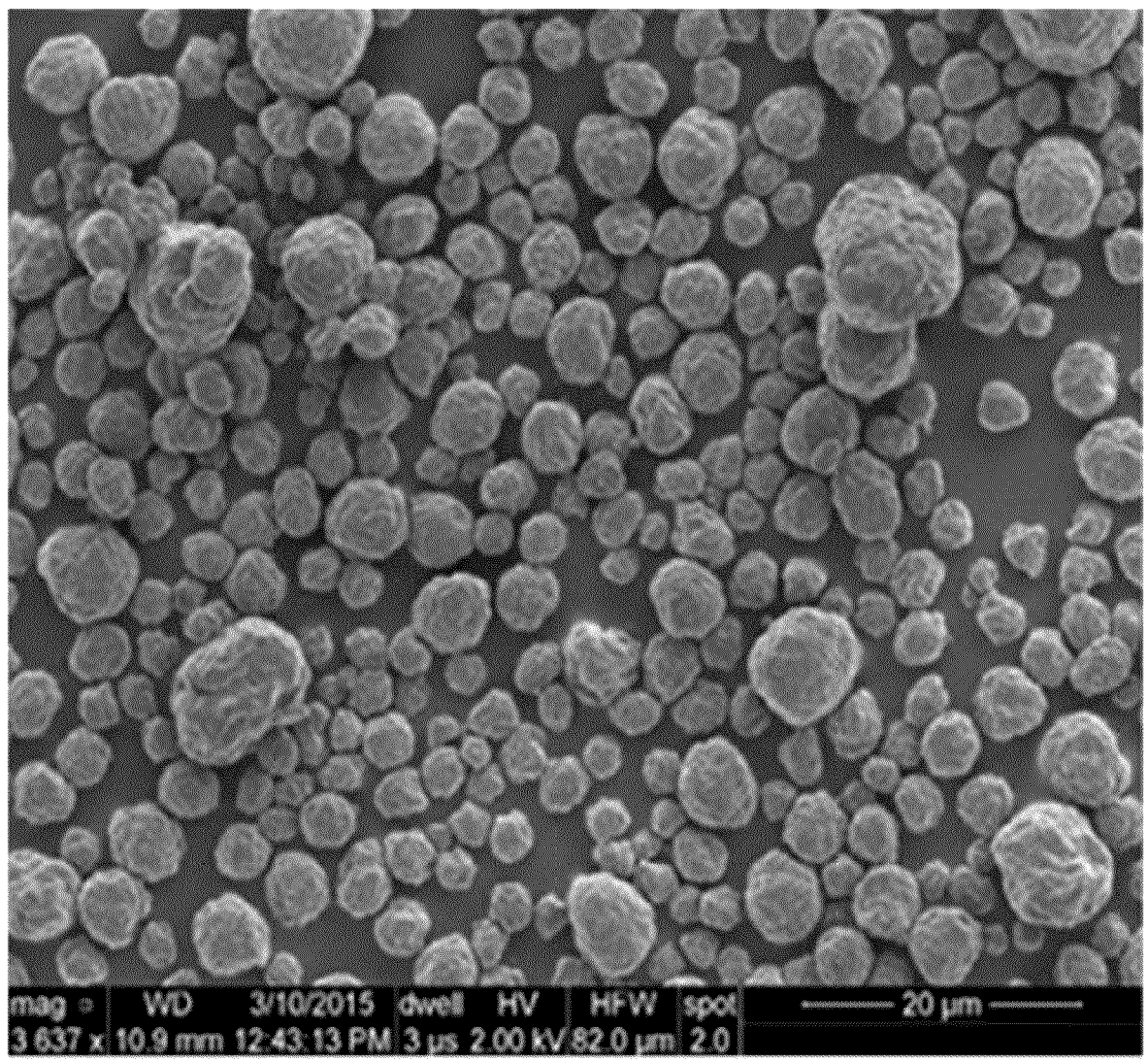
FIG. 4 is a scanning electron micrograph of pristine (white, undyed) spherical aggregates of polyelectrolyte-coated nanocrystalline cellulose.

FIG. 4 is the scanning electron micrograph of the pristine (white, undyed) spherical aggregate of polyelectrolyte-coated nanocrystalline cellulose.

Figure 10:
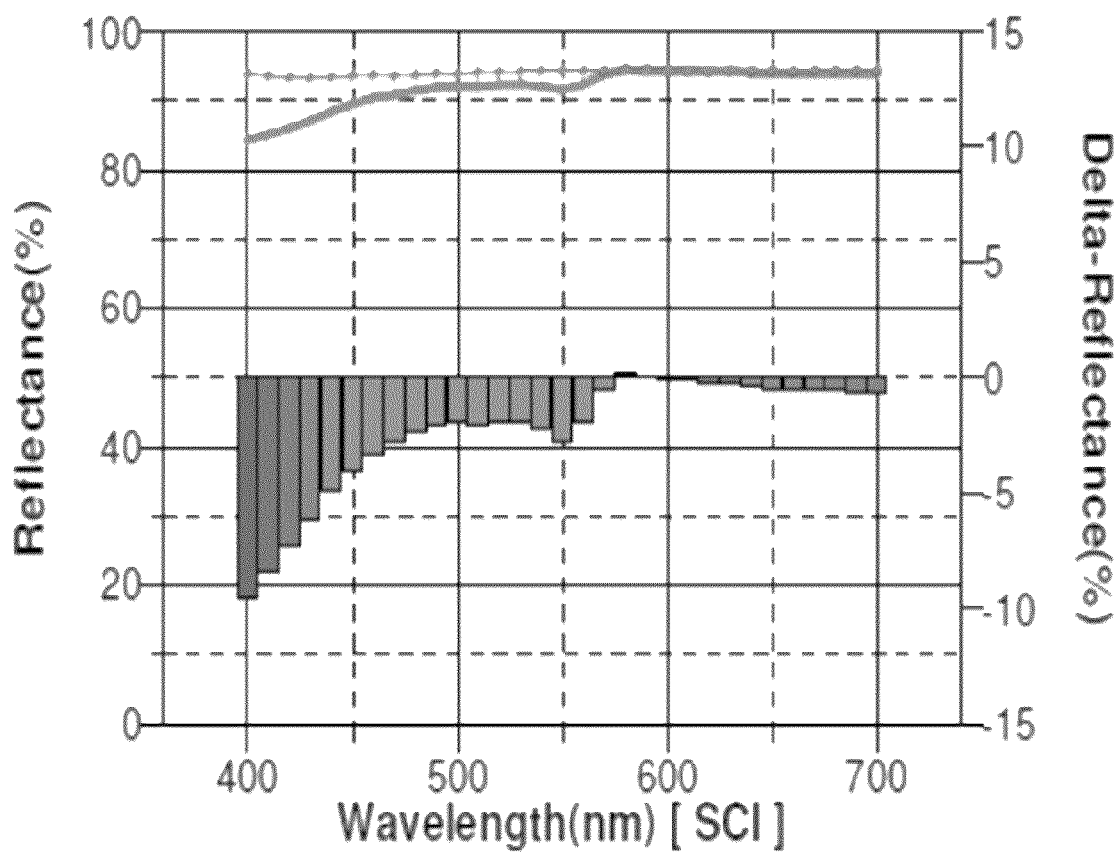
FIG. 10 is the reflectance spectrum of pristine (white, undyed) spherical aggregates of polyelectrolyte-coated nanocrystalline cellulose.

FIG. 10 is the reflectance spectrum of the pristine (white, undyed) spherical aggregate of polyelectrolyte-coated nanocrystalline cellulose.

Example 2—Production of a Red NCC Pigment

A beaker containing 1 L of the above NCC+ (0.5% w/v, 5 g) was fixed under a Rayneri mixer. The suspension was rapidly mixed while slowly adding a 100 mL solution of phloxine B (D&C Red 28) dye dissolved in water (0.5% w/v, 0.5 g). Stirring was continued for an additional 20 minutes.

Spray drying was performed by using an SD 3.5 Pilot Plant spray dryer on-site at Techni Process North America Inc. The inlet temperature was set to 175° C., with an outlet temperature of 68° C. Compressed air pressure was set at 50 psi resulting in approximately 10 L/h of feed flow to the dryer.

Figure 5:
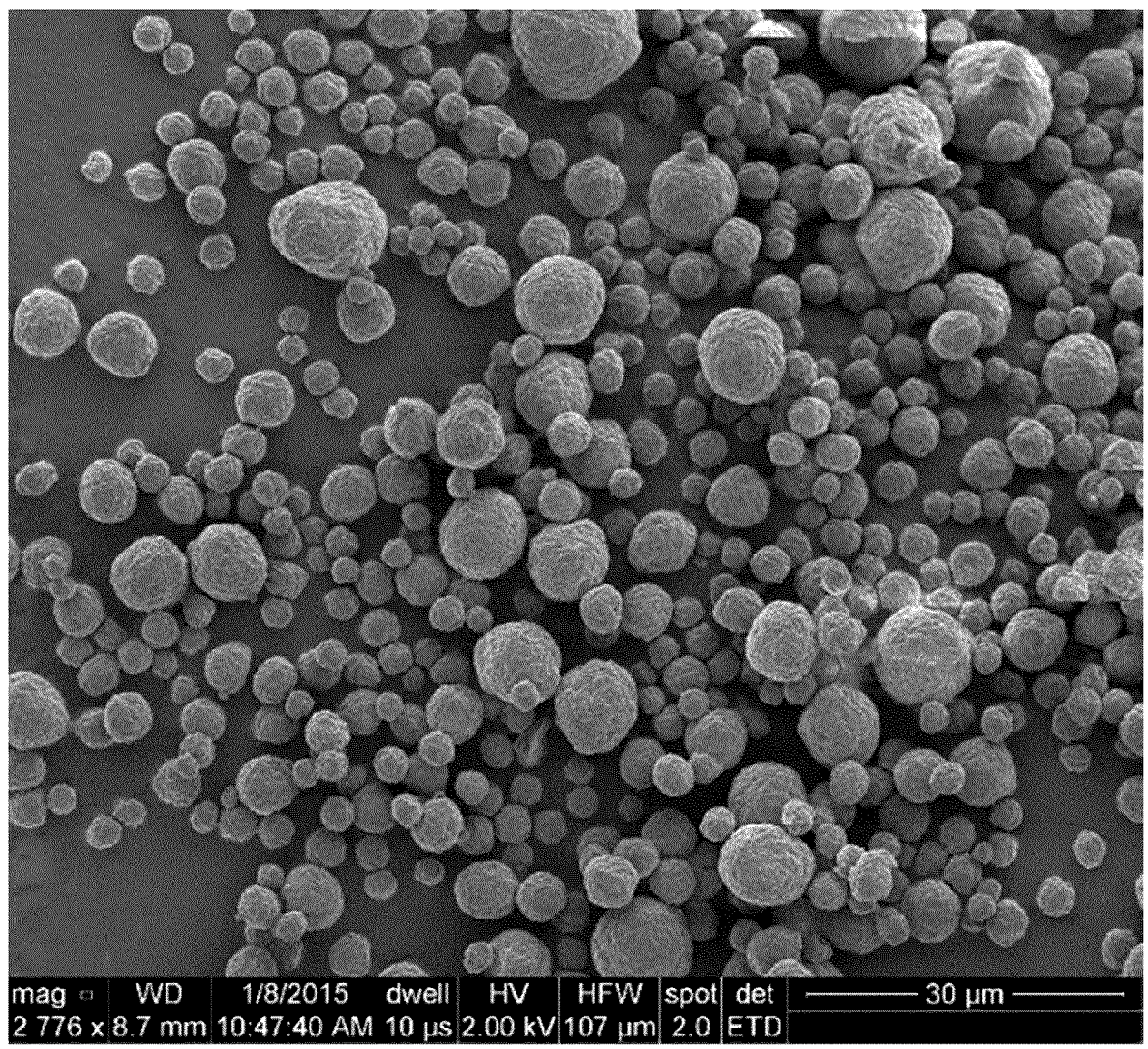
FIG. 5 is a scanning electron micrograph of spherical aggregates of the polyelectrolyte-coated nanocrystalline cellulose containing red dye #28.

Scanning electron microscopy (FIG. 5) of the red pigment reveals spherical shaped particles.

Figure 11:
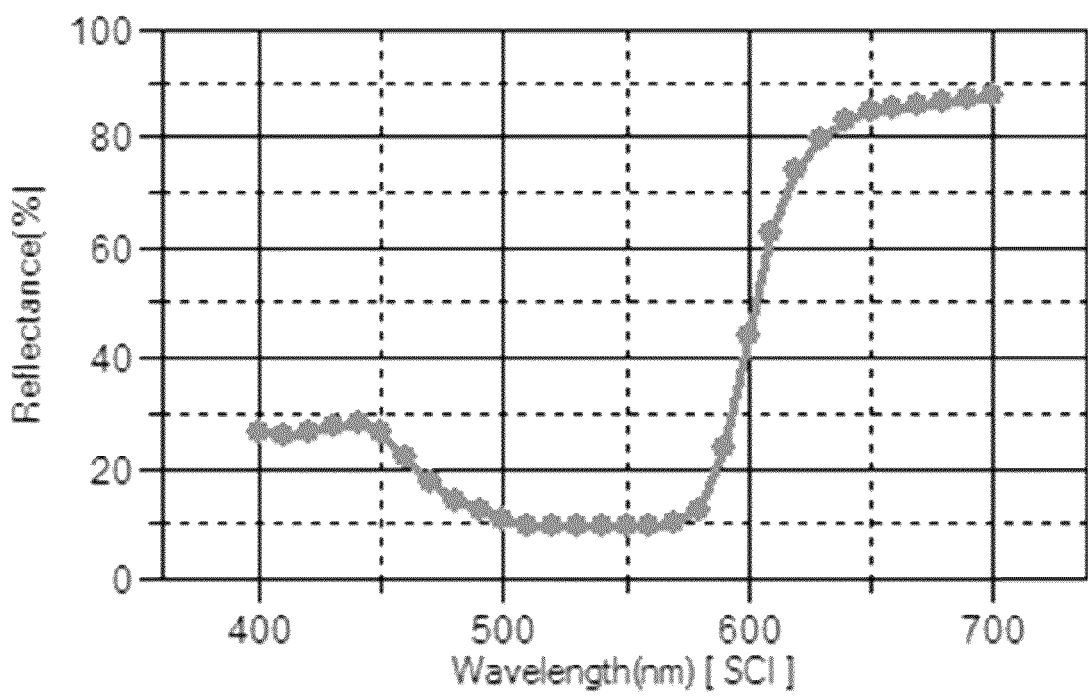
FIG. 11 is the reflectance spectrum of spherical aggregates of the polyelectrolyte-coated nanocrystalline cellulose containing red dye #28.

FIG. 11 is the reflectance spectrum of the spherical aggregate of polyelectrolyte-coated nanocrystalline cellulose containing red dye #28.

The resulting powder exhibits a vibrant color, good spreadability when applied to the skin, good adhesion on the skin and a fresh light feel on the skin.

Example 3—Production of a Blue NCC Pigment

A beaker containing 1 L of the above NCC+ (0.5% w/v, 5 g) was fixed under a Rayneri mixer. The suspension was rapidly mixed while slowly adding a 100 mL solution of FD&C blue dye #1 dissolved in water (0.5% w/v, 0.5 g). Stirring was continued for an additional 20 minutes.

Spray drying was performed by using an SD 3.5 Pilot Plant spray dryer on-site at Techni Process North America Inc. The inlet temperature was set to 175° C., with an outlet temperature of 68° C. Compressed air pressure was set at 50 psi resulting in approximately 10 L/h of feed flow to the dryer.

Figure 6:
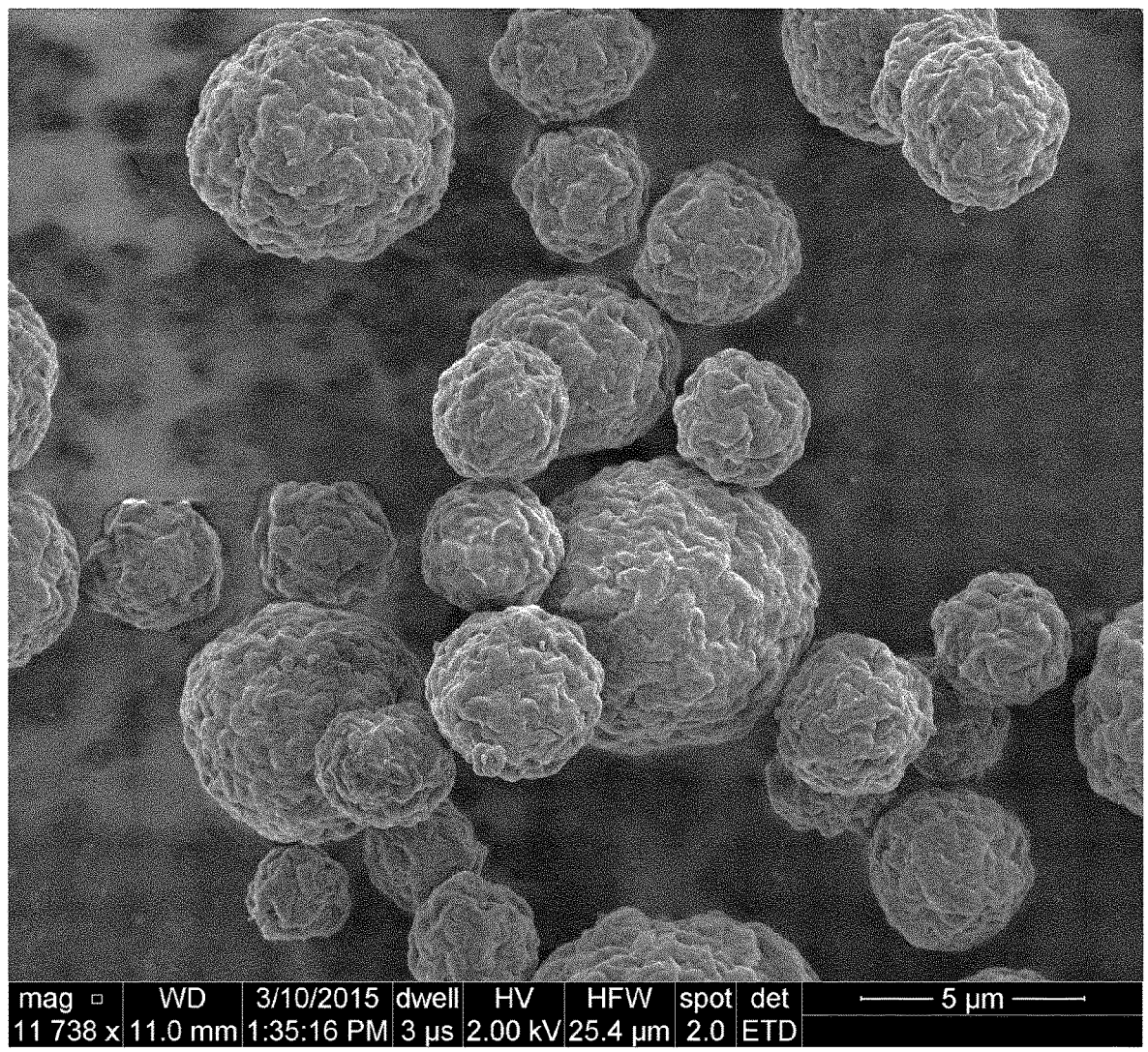
FIG. 6 is a scanning electron micrograph of spherical aggregates of the polyelectrolyte-coated nanocrystalline cellulose containing FD&C blue dye #1.

Scanning electron microscopy (FIG. 6) of the blue pigment reveals spherical shaped particles.

Figure 12:
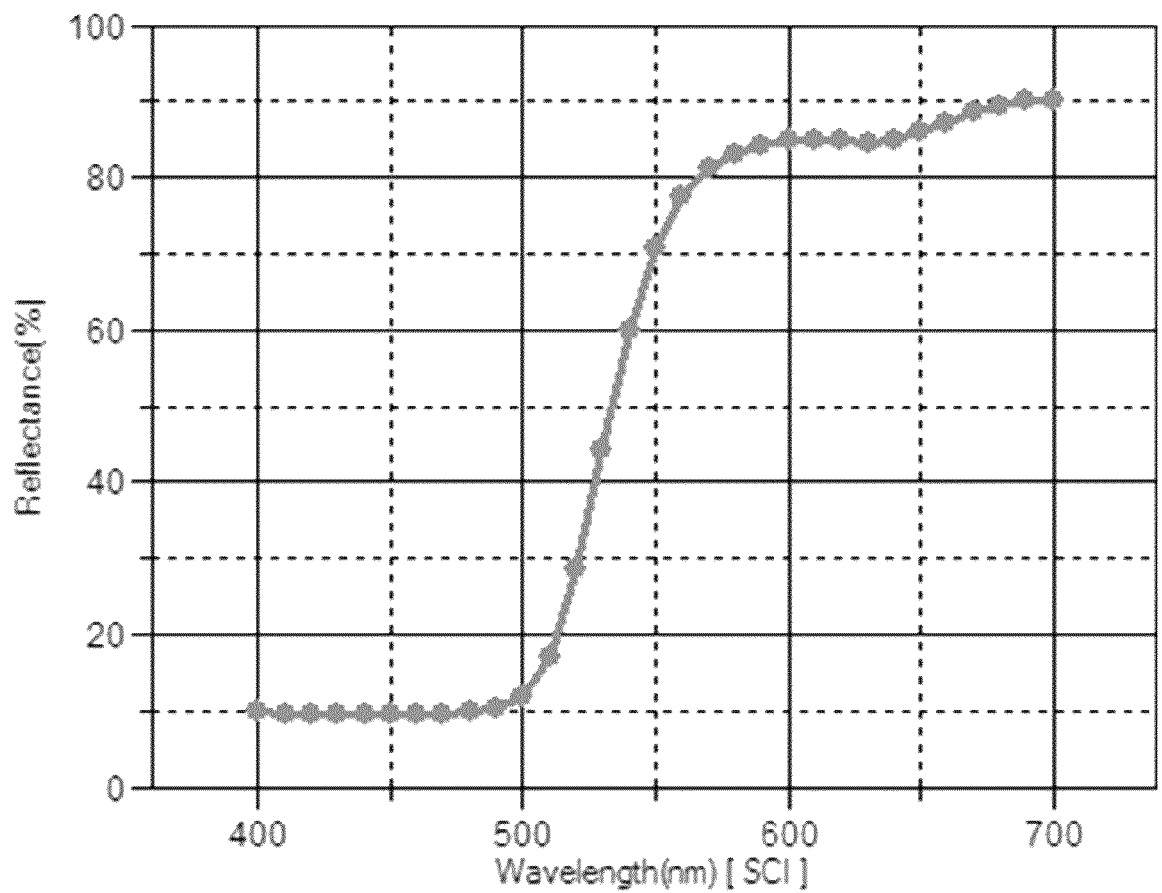
FIG. 12. Is the reflectance spectrum of spherical aggregates of the polyelectrolyte-coated nanocrystalline cellulose containing FD&C blue dye #1.

FIG. 12 is the reflectance spectrum of the spherical aggregate of polyelectrolyte-coated nanocrystalline cellulose containing FD&C blue dye #1.

The resulting powder exhibits a vibrant color, good spreadability when applied to the skin, good adhesion on the skin and a fresh light feel on the skin.

Example 4—Production of a Yellow NCC Pigment

A beaker containing 1 L of the above NCC+ (0.5% w/v, 5 g) was fixed under a Rayneri mixer. The suspension was rapidly mixed while slowly adding a 100 mL solution of FD&C yellow dye #5 dissolved in water (0.5% w/v, 0.5 g). Stirring was continued for an additional 20 minutes.

Spray drying was performed by using an SD 3.5 Pilot Plant spray dryer on-site at Techni Process North America Inc. The inlet temperature was set to 175° C., with an outlet temperature of 68° C. Compressed air pressure was set at 50 psi resulting in approximately 10 L/h of feed flow to the dryer.

Figure 7:
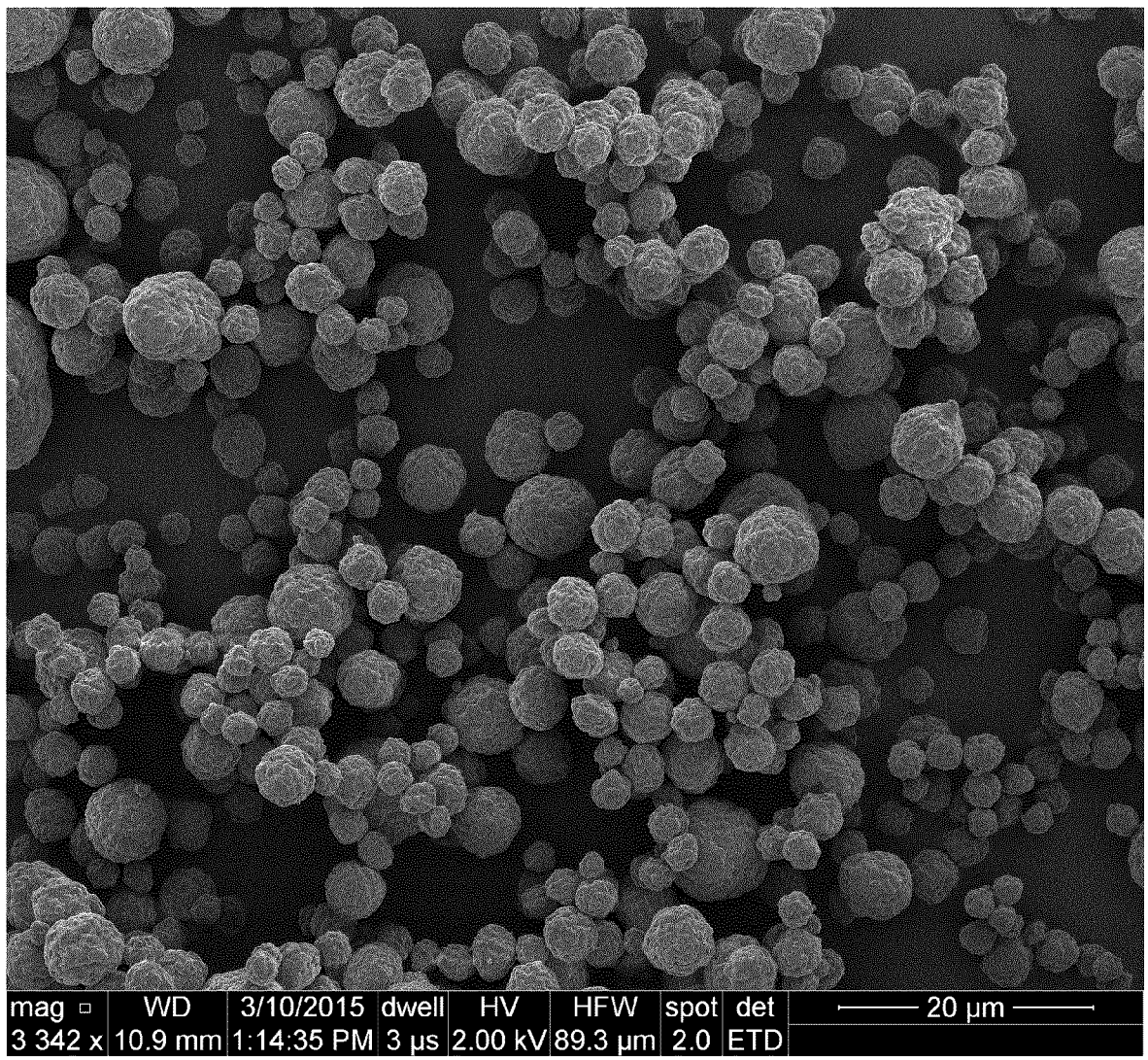
FIG. 7 is a scanning electron micrograph of spherical aggregates of the polyelectrolyte-coated nanocrystalline cellulose containing FD&C yellow dye #5.

Scanning electron microscopy (FIG. 7) of the blue pigment reveals spherical shaped particles.

Figure 13:
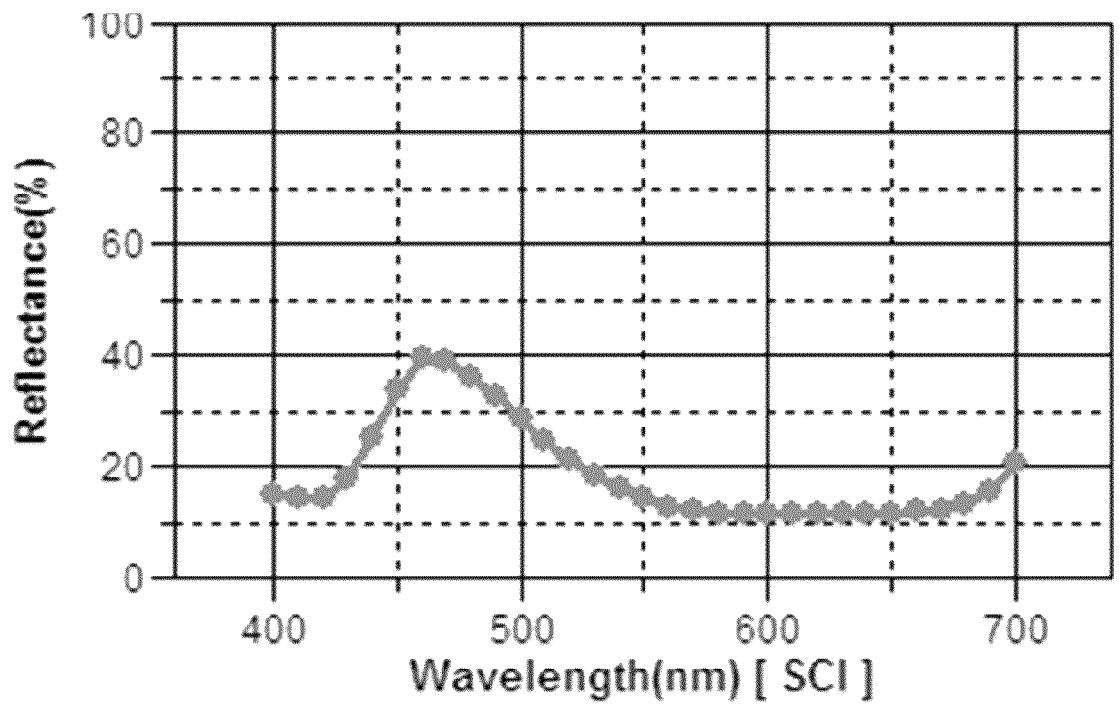
FIG. 13 is the reflectance spectrum of spherical aggregates of the polyelectrolyte-coated nanocrystalline cellulose containing FD&C yellow dye #5.

FIG. 13 is the reflectance spectrum of the spherical aggregate of polyelectrolyte-coated nanocrystalline cellulose containing FD&C blue dye #1.

The resulting powder exhibits a vibrant color, good spreadability when applied to the skin, good adhesion on the skin and a fresh light feel on the skin.

Example 5—Production of a Green NCC Pigment

The aqueous suspension of blue pigment from Example 3 and the aqueous suspension of yellow pigment from Example 4 were combined in a one-to-one ratio and stirred.

Spray drying was performed using a Buchi spray dryer. The inlet temperature was set to 175° C., with an outlet temperature of 68° C.

Figure 8:
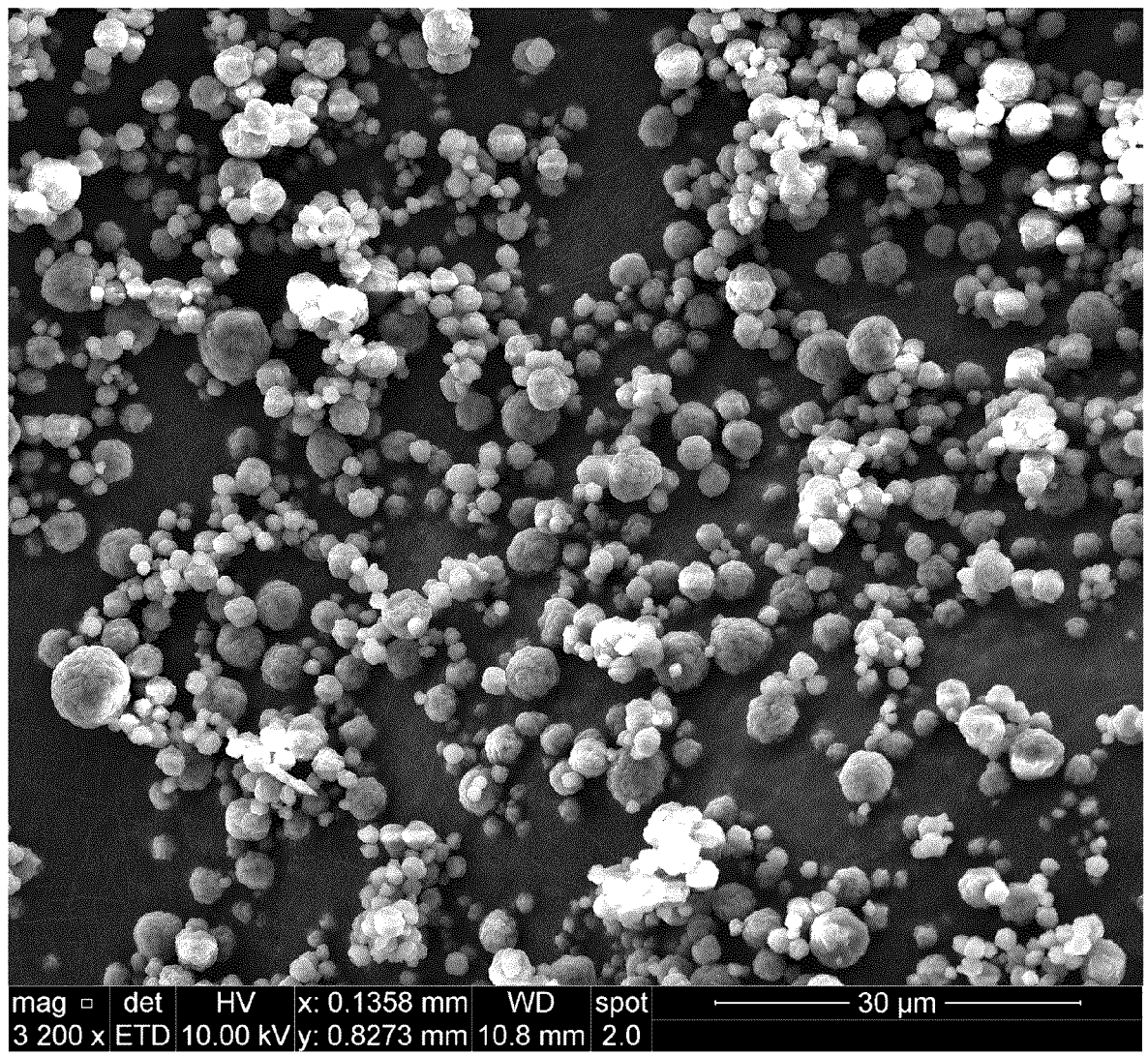
FIG. 8 is a scanning electron micrograph of spherical aggregates of the polyelectrolyte-coated nanocrystalline cellulose containing FD&C blue dye #1 and FD&C yellow dye #5 mixed 50:50 and spray dried to make a green pigment.

Scanning electron microscopy (FIG. 8) of the green pigment reveals spherical shaped particles.

Figure 14:
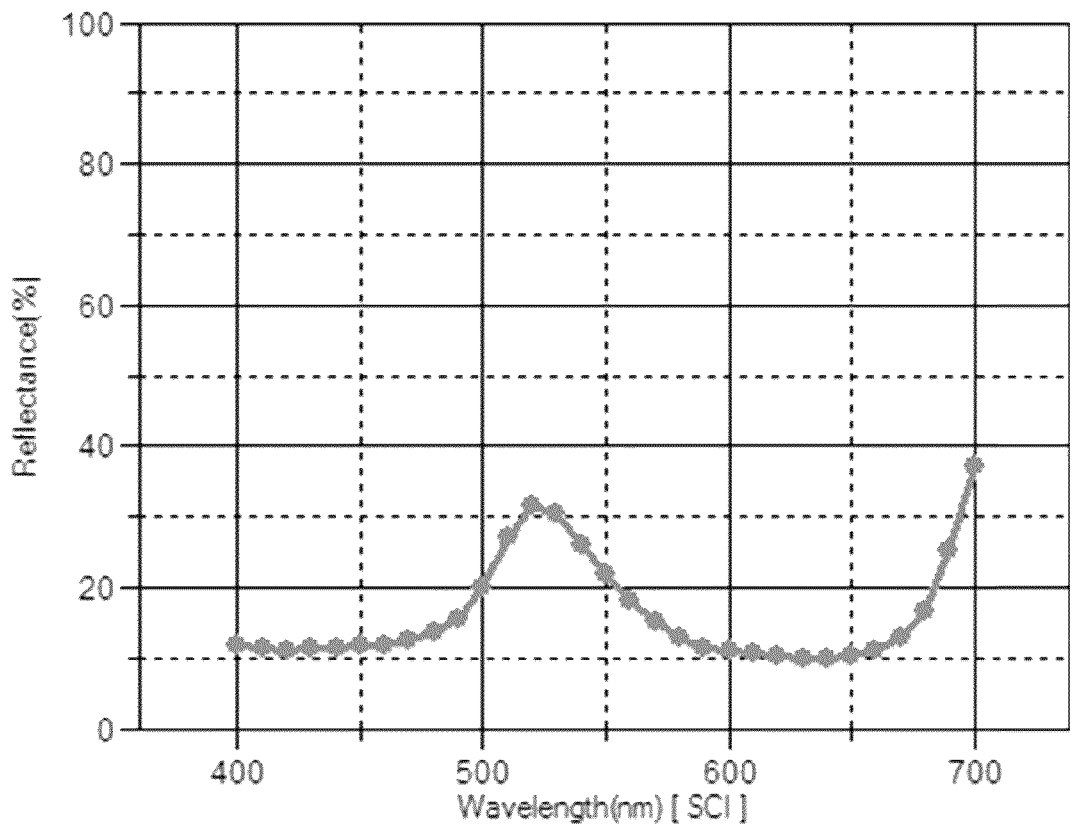
FIG. 14 is the reflectance spectrum of spherical aggregates of the polyelectrolyte-coated nanocrystalline cellulose containing FD&C blue dye #1 and FD&C yellow dye #5 mixed 50:50 and spray dried to make a green pigment.

FIG. 14 is the reflectance spectrum of the spherical aggregate of polyelectrolyte-coated nanocrystalline cellulose pigment containing FD&C blue dye #1 and FD&C yellow dye #5.

The resulting powder exhibits a vibrant color, good spreadability when applied to the skin, good adhesion on the skin and a fresh light feel on the skin.

Example 6—Cosmetic Formulation 50 mg of the red 28 NCC pigment of Example 2 was thoroughly mechanically mixed with 1 g of a proprietary cosmetic clear lip gloss base. Particles were well dispersed throughout the formulation without aggregation.

Optical microscopy revealed that the spherical shape of the pigments remained unaltered after 2 months at room temperature. Dye was not observed to leach from the pigment particles into the cosmetic oils.

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:
Nishikata et al., Cosmetics and Toiletries, 112, 39-55, 1997
G. Baranoski and A. Krishnaswamy, An Introduction to Light Interaction with Human Skin, Revista de Informatica Teorica e Aplicada (RITA) XI, no. 1, 2004, 33-60
JP 62-288662
JP 11-139926
JP 11-335240
U.S. Pat. No. 854,216 B2
DE 199 29 109
WO 00/15720

The invention claimed is:

1. A pigment comprising dyed crystalline cellulose particles comprising:
   a crystalline cellulose core having a surface charge, the crystalline cellulose being nanocrystalline cellulose or microcrystalline cellulose,
   one or more polyelectrolyte layers with alternating charges electrostatically adsorbed on top of each other on the crystalline cellulose core, the polyelectrolyte layer closest to the core having a charge opposite the surface charge of the core, and
   at least one organic dye having a charge,
wherein:
A) when the charge of the organic dye is opposite the surface charge of the crystalline cellulose core, the organic dye is electrostatically adsorbed on an even number of polyelectrolyte layers with alternating charges, and
B) when the charge of the organic dye is the same as the surface charge of the crystalline cellulose core, the organic dye is electrostatically adsorbed on an odd number of polyelectrolyte layers with alternating charges,
wherein sufficient dye is adsorbed on the one or more polyelectrolyte layers for the pigment to impart color to a medium in which it is incorporated,
wherein the crystalline cellulose core, the one or more polyelectrolyte layers, and the dye are strong adsorbed together so that the pigment is stable, wherein the dyed crystalline cellulose particles are aggregated together into solid spherical aggregates having an average size up to about 50 microns, and
wherein the aggregates are suspended in a fluid to which they impart color.

2. The pigment of claim 1, wherein the charge of the organic dye is opposite the surface charge of the crystalline cellulose core and the organic dye is adsorbed on an even number of polyelectrolyte layers with alternating charges adsorbed on top of each other on the crystalline cellulose core, the polyelectrolyte layer closest to the core having a charge opposite the surface charge of the core.

3. The pigment of claim 1, wherein the charge of the organic dye is the same as the surface charge of the crystalline cellulose core and the organic dye is adsorbed on an odd number of polyelectrolyte layers with alternating charges adsorbed on top of each other on the crystalline cellulose core, the polyelectrolyte layer closest to the core having a charge opposite the surface charge of the core.

4. The pigment of claim 1, wherein the crystalline cellulose is positively-charged microcrystalline cellulose that is microcrystalline cellulose modified with glycidyltrimethylammonium chloride functional groups, or with adsorbed cationic amylopectin.

5. The pigment of claim 1, wherein the crystalline cellulose is negatively-charged microcrystalline cellulose that is microcrystalline cellulose with phosphate and polyphosphate functional groups, carboxymethylcellulose sodium salt, carboxymethyl cellulose sodium sulfate salt, and microcrystalline cellulose reacted with calcium alginate.

6. The pigment of claim 1, wherein the crystalline cellulose is positively-charged nanocrystalline cellulose that is nanocrystalline cellulose with glycidyltrimethylammonium chloride functional groups, nanocrystalline cellulose reacted cationic surfactant hexadecyltrimethylammonium or cationic polyacrylamide or nanocrystalline cellulose grafted with a cationic polymer.

7. The pigment of claim 1, wherein the crystalline cellulose is negatively charged nanocrystalline cellulose that is carboxylated nanocrystalline cellulose, sulfonated nanocrystalline cellulose, phosphonated nanocrystalline cellulose, or a salt thereof.

8. The pigment of claim 1, wherein the dyed crystalline cellulose comprises a negatively-charged polyelectrolyte.

9. The pigment of claim 1, wherein the dyed crystalline cellulose comprises a positively-charged polyelectrolyte that is a copolymer of acrylamide with an aminoderivative of acrylic acid or methacrylic acid ester; quaternized poly-4-vinylpyridine; poly-2-methyl-5-vinylpyridine; poly(ethyleneimine); pol-L-lysine, a poly(amidoamine); a poly(amino-co-ester), or a polyquaternium.

10. The pigment of claim 1, wherein the dyed crystalline cellulose particles are mixed with undyed crystalline cellulose particles comprising:
  the crystalline cellulose core, and
  optionally one or more polyelectrolyte layers with alternating charges adsorbed on top of each other on the crystalline cellulose core, the polyelectrolyte layer closest to the core having a charge opposite the surface charge of the core,
wherein the undyed crystalline cellulose particles are free of dyes.

11. The pigment of claim 1, comprising a mixture of dyed crystalline cellulose particles of at least two different hues.

12. The pigment of claim 1, wherein the fluid is a cosmetically acceptable auxiliary agent.

13. A method of producing a pigment of claim 1, the method comprising the steps of:
  a) providing crystalline cellulose cores having a surface charge, an organic dye having a charge, a first polyelectrolyte having a charge opposite to the charge of the crystalline cellulose cores, and optionally a second polyelectrolyte having the same charge as the crystalline cellulose cores, the crystalline cellulose being nanocrystalline cellulose or microcrystalline cellulose,
  when the charge of the organic dye is opposite the surface charge of the crystalline cellulose core,
  b) adsorbing an even number of polyelectrolyte layers with alternating charges on top of each other on the crystalline cellulose core, and then
  c) adsorbing the organic dye on the crystalline cellulose core, thereby producing the pigment,
  or when the charge of the organic dye is the same as the surface charge of the crystalline cellulose core
  b') adsorbing an odd number of polyelectrolyte layers with alternating charges on top of each other on the crystalline cellulose core, and then
  c') adsorbing the organic dye on the crystalline cellulose core, thereby producing the pigment,
  spray-drying the dyed crystalline cellulose particles, thereby aggregating the dyed crystalline cellulose particles into solid spherical aggregates having an average size up to about 50 microns, and
  suspending the aggregates in a fluid thereby imparting color to said fluid,
  wherein the polyelectrolyte layer closest to the core has a charge opposite the surface charge of the core.

14. The method of claim 13, wherein step b) comprises:
  b1) suspending the crystalline cellulose cores in a liquid in which the first polyelectrolyte is soluble, adding the first polyelectrolyte to the suspension, thereby adsorbing the first polyelectrolyte on the surface of the crystalline cellulose core,
  b2) isolating the crystalline cellulose cores,
  b3) suspending the crystalline cellulose cores in a liquid in which the second polyelectrolyte is soluble, adding the second polyelectrolyte to the suspension, thereby adsorbing the second polyelectrolyte on the surface of the crystalline cellulose core, and
  b4) isolating the crystalline cellulose cores, and
  b5) optionally repeating all of steps b1) to b4) one or more times.

15. The method of claim 13, wherein step b') comprises:
  b'1) suspending the crystalline cellulose cores in a liquid in which the first polyelectrolyte is soluble, adding the first polyelectrolyte to the suspension, thereby adsorbing the first polyelectrolyte on the surface of the crystalline cellulose core, and
  b'2) isolating the crystalline cellulose cores.

16. The method of claim 15, wherein step b') further comprises:
  b'3) suspending the crystalline cellulose cores in a liquid in which the second polyelectrolyte is soluble, adding the second polyelectrolyte to the suspension, thereby adsorbing the second polyelectrolyte on the surface of the crystalline cellulose core,
  b'4) isolating the crystalline cellulose cores,
  b'5) optionally, suspending the crystalline cellulose cores in a liquid in which the first polyelectrolyte is soluble, adding the first polyelectrolyte to the suspension, thereby adsorbing the first polyelectrolyte on the surface of the crystalline cellulose core,
  b'6) isolating the crystalline cellulose cores, and
  b'7) optionally repeating all of steps b'3) to b'6) one or more times.

17. The method of claim 13, wherein steps c) and/or c') comprise the steps of suspending the crystalline cellulose cores in a liquid in which the dye is soluble, and adding the dye to the suspension, thereby adsorbing the organic dye directly on the surface of the crystalline cellulose core.

18. The method of claim 13, further comprising the step f) of mixing the dyed crystalline cellulose particles with undyed crystalline cellulose particles, the undyed crystalline cellulose particles comprising:
  the crystalline cellulose core, and
  optionally one or more polyelectrolyte layers with alternating charges adsorbed on top of each other on the crystalline cellulose core, the polyelectrolyte layer closest to the core having a charge opposite the surface charge of the core,
the undyed crystalline cellulose particles being free of dyes.

19. The method of claim 13, further comprising the step of mixing the dyed crystalline cellulose particles with dyed crystalline cellulose particles of a different hue.

20. The method of claim 13, wherein the fluid is a cosmetically acceptable auxiliary agent.

* * * * *